United States Patent
Ito et al.

(10) Patent No.: US 12,235,232 B2
(45) Date of Patent: Feb. 25, 2025

(54) GAS SENSOR, METHOD OF MANUFACTURING GAS SENSOR, AND FUEL CELL VEHICLE

(71) Applicant: Nuvoton Technology Corporation Japan, Kyoto (JP)

(72) Inventors: Satoru Ito, Hyogo (JP); Kazunari Homma, Gifu (JP); Koichi Kawashima, Kyoto (JP); Koji Katayama, Nara (JP); Shinichi Yoneda, Kyoto (JP)

(73) Assignee: NUVOTON TECHNOLOGY CORPORATION JAPAN, Kyoto (JP)

( * ) Notice: Subject to any disclaimer, the term of this patent is extended or adjusted under 35 U.S.C. 154(b) by 694 days.

(21) Appl. No.: 17/459,262

(22) Filed: Aug. 27, 2021

(65) Prior Publication Data
US 2021/0389264 A1  Dec. 16, 2021

Related U.S. Application Data

(63) Continuation of application No. PCT/JP2020/000803, filed on Jan. 14, 2020.

(30) Foreign Application Priority Data

Mar. 7, 2019 (JP) .................... 2019-042012

(51) Int. Cl.
*G01N 27/12* (2006.01)
*B60K 15/03* (2006.01)
*B60L 50/70* (2019.01)

(52) U.S. Cl.
CPC ....... *G01N 27/12* (2013.01); *B60K 15/03006* (2013.01); *B60L 50/70* (2019.02); *B60K 2015/03315* (2013.01)

(58) Field of Classification Search
CPC .... G01N 27/12; G01N 27/125; G01N 33/005; B60K 15/03006; B60K 2015/03315;
(Continued)

(56) References Cited

U.S. PATENT DOCUMENTS 7,356,420 B2 * 4/2008 Vilanova ............... G01N 33/146
702/22
2007/0054170 A1 * 3/2007 Isenberg ................ H01B 1/122
429/495

(Continued)

FOREIGN PATENT DOCUMENTS

| JP | S59-058348 A | 4/1984 | |
|---|---|---|---|
| WO | 2013/051267 A1 | 4/2013 | |
| WO | WO-2017037984 A1 * | 3/2017 | ........... B60K 15/063 |

OTHER PUBLICATIONS

International Search Report and Written Opinion issued on Mar. 24, 2020 in International Patent Application No. PCT/JP2020/000803; with partial English translation.
(Continued)

*Primary Examiner* — Joseph J Dallo
(74) *Attorney, Agent, or Firm* — Rimon P.C.

(57) ABSTRACT

A gas sensor includes a gas detecting element that includes a first electrode, a metal oxide layer, and a second electrode; and a first insulating film that has an opening allowing the second electrode to be partially exposed therethrough and covers the first electrode, the metal oxide layer, and another part of the second electrode. The metal oxide layer has a characteristic where its resistance value changes as the second electrode makes contact with gas molecules including hydrogen atoms. A first step is provided at a portion lying on an interface between the metal oxide layer and the second electrode and located within the opening as viewed in plan view. A local region is provided in the metal oxide layer and near the first step. A degree of oxygen deficiency of the local
(Continued)

region is greater than a degree of oxygen deficiency of other regions in the metal oxide layer.

13 Claims, 18 Drawing Sheets

(58) Field of Classification Search
CPC .. B60K 1/00; B60K 15/07; B60K 2001/0411; B60K 2015/0638; B60L 50/70; B60L 50/72; B60Y 2400/202; Y02E 60/50; Y02T 90/40; H01M 8/00; H01M 8/04
See application file for complete search history.

(56) References Cited

U.S. PATENT DOCUMENTS

| | | | |
|---|---|---|---|
| 2009/0301898 A1* | 12/2009 | Backhaus-Ricoult | ....................... H01M 4/8605 205/724 |
| 2013/0202489 A1* | 8/2013 | Ong | ...................... G01N 33/005 977/902 |
| 2013/0250658 A1 | 9/2013 | Wei et al. | |
| 2017/0131227 A1* | 5/2017 | Homma | ............... H01M 8/0444 |
| 2017/0241933 A1* | 8/2017 | Fujii | ..................... G01N 33/005 |
| 2017/0269043 A1* | 9/2017 | Homma | ............... G01N 33/005 |
| 2017/0307556 A1* | 10/2017 | Muraoka | ............. G01N 33/0031 |
| 2017/0307557 A1* | 10/2017 | Muraoka | ............... G01N 27/125 |

OTHER PUBLICATIONS

J.Yu et al., "Hydrogen gas sensing properties of Pt/Ta2O5 Schottky diodes based on Si and SiC substrates," Sensors and Actuators A 172 (2011) pp. 9-14.

Toshiyuki Usagawa et al., "A Novel Pt—Ti—O Gate Si-Metal-Insulator-Semiconductor Field-Effect Transistor Hydrogen Gas Sensor," IEEE Sensors 2010 Conference, pp. 2145-2148.

Ikuo Takahashi, "Catalytic Combustion Type Hydrogen Gas Sensor," Journal of the Surface Finishing Society of Japan, vol. 57, No. 4, 2006, pp. 267-270; with parcial English translation.

Hisao Kitaguchi, "The present situation and some subjects of the hydrogen gas sensor," Hydrogen Energy Systems, vol. 30, No. 2, 2005, pp. 35-40; with English abstract.

* cited by examiner

GAS SENSOR, METHOD OF MANUFACTURING GAS SENSOR, AND FUEL CELL VEHICLE

CROSS REFERENCE TO RELATED APPLICATIONS

This is a continuation application of PCT International Application No. PCT/JP2020/000803 filed on Jan. 14, 2020, designating the United States of America, which is based on and claims priority of Japanese Patent Application No. 2019-042012 filed on Mar. 7, 2019. The entire disclosures of the above-identified applications, including the specifications, drawings and claims are incorporated herein by reference in their entirety.

FIELD

The present disclosure relates to a gas sensor, a method of manufacturing the gas sensor, and a fuel cell vehicle provided with the gas sensor.

BACKGROUND

Nowadays, vigorous efforts are being made in various fields toward realizing a hydrogen-powered society. In particular, hydrogen-fueled fuel cell vehicles that are expected to be the ultimate environmentally friendly vehicles have been released into the market, and as such, infrastructures such as hydrogen stations are steadily being made available. Such circumstances have led to increased importance of sensors that detect hydrogen to ensure the safety and the comfort in a hydrogen-powered society.

Among sensors that detect a gas represented by hydrogen, there is known a gas sensor that includes a gas detecting element of a metal-insulator-metal (MIM) structure, in which a gas sensitive insulating film (also referred to below simply as an insulating film) and metal films are laminated together.

Such a gas sensor can be used to detect, for example, hydrogen, alcohol, hydrocarbon, ammonia, or amine contained in a trace amount in a gas, and such a gas sensor can detect, in particular, a highly reactive gas, such as hydrogen, with high efficiency.

PTL 1 discloses a gas sensor of the MIM structure, in which an insulating film and metal films are laminated together. In the gas sensor disclosed in PTL 1, an insulating film obtained by adding a predetermined amount of palladium and glass to tantalum pentoxide ($Ta_2O_5$) is used, and platinum (Pt) is used as an upper and a lower metal electrode that sandwich the insulating film.

CITATION LIST

Patent Literature

PTL 1: Japanese Unexamined Patent Application Publication No. S59-058348

Non Patent Literature

NPL 1: J. Yu et al. "Hydrogen gas sensing properties of Pt/Ta2O5 Schottky Diodes based on Si and SiC substrates." Sensors and Actuators A 172 (2011) pp. 9-14

NPL 2: Toshiyuki Usagawa et al. "A Novel Pt—Ti—O Gate Si-Metal-Insulator-Semiconductor Field-Effect Transistor." IEEE SENSORS 2010 Conference, pp. 2145-2148

NPL 3: Ikuo Takahashi, "Catalytic Combustion Type Hydrogen Gas Sensor," Journal of The Surface Finishing Society of Japan, Vol. 57, No. 4, 2006, pp. 267-270

NPL 4: Hisao Kitaguchi, "The present situation and some subjects of the hydrogen gas sensor," Hydrogen Energy Systems, Vol. 30, No. 2 (2005), pp. 35-40

SUMMARY

Technical Problem

Despite the above, with the existing gas detecting elements, the gas detecting elements are heated to 100° C. or higher in order to improve the sensitivity for detecting a gas containing hydrogen atoms, for example, and the required power consumption of even the smallest gas detecting element is around 100 mW. Accordingly, when such a gas detecting element is kept ON during use, the gas detecting element disadvantageously consumes a very large amount of power.

The present disclosure provides a gas sensor that is less power consuming and is capable of detecting a gas molecule containing a hydrogen atom stably and with high sensitivity. The present disclosure further provides a method of manufacturing such a gas sensor and a fuel cell vehicle.

Solution to Problem

To address the existing problem, a gas sensor according to one aspect of the present disclosure includes: a gas detecting element that includes a first electrode, a metal oxide layer provided on the first electrode, and a second electrode provided on the metal oxide layer, the gas detecting element detecting a gas molecule existing in a gas and including a hydrogen atom; and a first insulating film having an opening that allows a part of the second electrode to be exposed therethrough, the first insulating film covering the first electrode, the metal oxide layer, and another part of the second electrode, wherein the metal oxide layer has a characteristic in which a resistance value of the metal oxide layer changes when the second electrode comes into contact with the gas molecule, a first step is provided at a portion lying on an interface between the metal oxide layer and the second electrode and located within the opening as viewed in plan view, a local region is provided in the metal oxide layer and close to the first step, and a degree of oxygen deficiency of the local region is greater than a degree of oxygen deficiency of a region other than the local region in the metal oxide layer.

A method of manufacturing a gas sensor according to one aspect of the present disclosure includes: forming a first electrode film on a substrate; forming a metal oxide film on the first electrode film, the metal oxide film including an upper surface provided with a first step; forming a second electrode film on the metal oxide film; forming a gas detecting element including a first electrode, a metal oxide layer, and a second electrode by patterning the first electrode film, the metal oxide film, and the second electrode film so as to include the first step as viewed in plan view; forming a first insulating film so as to cover the gas detecting element; and forming an opening by removing a part of the first insulating film, the opening allowing a part of the second electrode on the first step to be exposed therethrough as viewed in plan view.

A fuel cell vehicle according to one aspect of the present disclosure includes: a passenger compartment; a gas tank compartment housing a hydrogen gas tank; a fuel cell compartment housing a fuel cell; and the gas sensor according to claim 1, wherein the gas sensor is provided in at least one of the gas tank compartment or the fuel cell compartment.

Advantageous Effects

The present disclosure can provide a gas sensor that is less power consuming and is capable of detecting a gas molecule containing a hydrogen atom stably and with high sensitivity. The present disclosure can further provide a method of manufacturing such a gas sensor and a fuel cell vehicle.

BRIEF DESCRIPTION OF DRAWINGS

These and other advantages and features will become apparent from the following description thereof taken in conjunction with the accompanying Drawings, by way of non-limiting examples of embodiments disclosed herein.

Figure 1A:
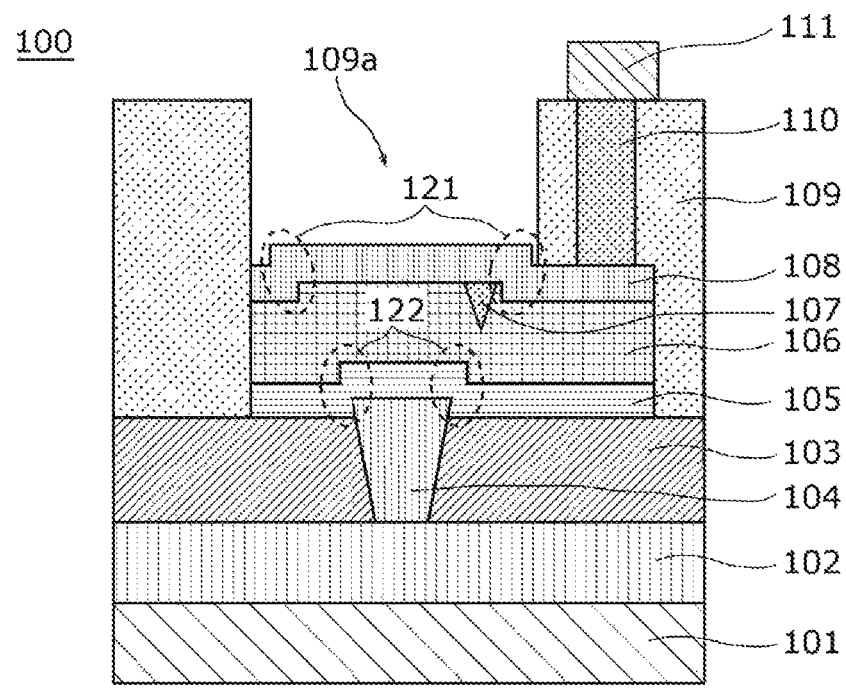
FIG. 1A is a cross-sectional view of a gas sensor according to Embodiment 1.

DESCRIPTION OF EMBODIMENTS (Underlying Knowledge Forming Basis of the Present Disclosure)

The present inventors have conducted diligent studies and thus found the following problems with existing gas sensors.

PTL 1 indicates that the disclosed gas sensor can detect an inflammable gas containing hydrogen but does not teach any detailed mechanism for such detection. Thus, with an assumption that a phenomenon similar to the mechanism disclosed in NPL 1 that concerns a gas sensor (Pt—Ta$_2$O$_5$—Si) of a metal-insulator-semiconductor (MIS) structure is also induced in the gas sensor disclosed in PTL 1, this mechanism can be described as follows.

First, when a gas containing a hydrogen gas, for example, has come into contact with a surface of platinum, which is a metal having a catalytic effect, the catalytic effect of the platinum causes the hydrogen gas to break down into hydrogen atoms, and these hydrogen atoms take oxygen atoms from the tantalum pentoxide in the insulating film in accordance with the chemical reaction formula shown below. Thus, an oxygen vacancy is formed in the tantalum pentoxide, and this conceivably allows a current to flow more easily.

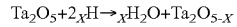

Meanwhile, when the gas containing the hydrogen gas ceases to exist on the surface of the platinum, the reverse process occurs in accordance with the chemical reaction formula shown below. Thus, the oxygen vacancy in the tantalum pentoxide ceases to exit, which conceivably makes the current flow less easily.

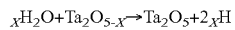

Based on such a mechanism, it is conceivable that the MIM structure in which an insulating film obtained by adding a predetermined amount of palladium and glass to tantalum pentoxide is used and platinum is used as an upper and a lower metal electrode that sandwich the insulating film functions as a gas sensor that detects a gas containing hydrogen atoms.

Moreover, in the gas sensor of the MIM structure described in PTL 1, a heater is provided adjacent to the gas detecting element. At the time of carrying out a measurement, a predetermined voltage is applied to the heater, and thus the temperature of the gas detecting element is raised to 400° C. This is conceivably for raising the detection sensitivity of the gas detecting element. In other words, although the hydrogen gas is dissociated into hydrogen atoms by use of platinum, which is a metal having a catalytic effect, since the rate of dissociating molecules containing hydrogen atoms into the hydrogen atoms through the catalytic effect is proportional to the rise in the temperature, it is considered that the detection sensitivity increases in accordance with the rise in the temperature of the gas detecting element.

Not only in the gas sensor of the MIM structure but also in a gas sensor of the MIS structure that utilizes the catalytic effect of a metal, a heater is provided adjacent to a gas detecting element, and the gas sensor is used normally with its surrounding temperature retained at 100° C. or higher. For example, in the gas sensor in which the MIS structure is used as a diode as disclosed in NPL 1 described above, the temperature of 100° C. or higher is required to carry out a detection. Moreover, the gas sensor in which the MIS structure is used as a transistor as disclosed in NPL 2 is made to operate with its surrounding temperature held at 115° C.

Furthermore, the contact combustion gas sensor disclosed in NPL 3 is also one of the gas sensors in which the catalytic effect of a metal is used, and in this contact combustion gas sensor as well, the gas detecting element is heated to 200° C. to 300° C. in operation.

Meanwhile, the hot wire semiconductor gas sensor and the thermal conduction gas sensor disclosed in NPL 4 are gas sensors in which the catalytic effect of a metal is not used, but even in these gas sensors, the gas detecting element is heated to 100° C. or higher.

In this manner, with the existing gas detecting elements, the gas detecting elements are heated to 100° C. or higher in order to improve the sensitivity for detecting a gas containing hydrogen atoms, and even the smallest gas detecting element consumes around 100 mW of power. Accordingly, when these gas detecting elements are kept ON during use, the gas detecting elements disadvantageously consume a very large amount of power.

A gas sensor according to one aspect of the present disclosure is capable of detecting a gas molecule containing a hydrogen atom stably and with high sensitivity and also excels in the power saving performance.

(Aspects of the Present Disclosure)

A gas sensor, a method of manufacturing a gas sensor, and a fuel cell vehicle according to some aspects of the present disclosure include features such as those described below.

A gas sensor according to one aspect of the present disclosure includes a gas detecting element and a first insulating film. The gas detecting element includes a first electrode, a metal oxide layer provided on the first electrode, and a second electrode provided on the metal oxide layer. The gas detecting element detects a gas molecule existing in a gas and including a hydrogen atom. The first insulating film has an opening that allows a part of the second electrode to be exposed therethrough. The first insulating film covers the first electrode, the metal oxide layer, and another part of the second electrode. The metal oxide layer has a characteristic in which a resistance value of the metal oxide layer changes as the second electrode comes into contact with the gas molecule. A first step is provided at a portion lying on an interface between the metal oxide layer and the second electrode and located within the opening as viewed in plan view. A local region is provided in the metal oxide layer and near the first step. A degree of oxygen deficiency of the local region is greater than a degree of oxygen deficiency of a region other than the local region in the metal oxide layer.

In the gas sensor according to one aspect of the present disclosure, the first step may have an upwardly convex shape.

The gas sensor according to one aspect of the present disclosure may further include a first contact plug provided between a substrate and the first electrode. The first contact plug may include a side surface surrounding the first contact plug, and the side surface may be covered by a second insulating film. The first contact plug may have an upper surface that projects from an upper surface of the second insulating film. The first electrode may include a second step provided across the upper surface of the first contact plug and the upper surface of the second insulating film surrounding the first contact plug. The first step may be a step resulting from a transfer of the second step onto an upper surface of the metal oxide layer.

In the gas sensor according to one aspect of the present disclosure, the first step may have a downwardly convex shape.

The gas sensor according to one aspect of the present disclosure may further include a first contact plug provided between a substrate and the first electrode. A side surface surrounding the first contact plug may be covered by a second insulating film. An upper surface of the first contact plug may be recessed from an upper surface of the second insulating film. The first electrode may include a third step provided across the upper surface of the first contact plug and the upper surface of the second insulating film surrounding the first contact plug. The first step may be a step resulting from a transfer of the third step onto an upper surface of the metal oxide layer.

In the gas sensor according to one aspect of the present disclosure, the second electrode may include a material having a catalytic effect of dissociating the gas molecule into the hydrogen atom.

In the gas sensor according to one aspect of the present disclosure, the second electrode may include platinum or palladium.

In the gas sensor according to one aspect of the present disclosure, the metal oxide layer may transition reversibly between a high-resistance state and a low-resistance state in accordance with a voltage applied across the first electrode and the second electrode.

The gas sensor according to one aspect of the present disclosure may further include a current detector that detects a current that flows in the metal oxide layer when a predetermined voltage is applied across the first electrode and the second electrode. A decrease in the resistance value may be detected based on an increase in the current detected by the current detector.

In the gas sensor according to one aspect of the present disclosure, the metal oxide layer may include a transition metal oxide.

In the gas sensor according to one aspect of the present disclosure, the transition metal oxide may be any one of tantalum oxide, hafnium oxide, or zirconium oxide.

The gas sensor according to one aspect of the present disclosure may further include a second contact plug penetrating through a part of a portion of the first insulating film where the first insulating film covers the second electrode and connected to the second electrode, and a conductor connected to the second contact plug at an upper side of the second contact plug.

A method of manufacturing a gas sensor according to one aspect of the present disclosure includes: forming a first electrode film on a substrate; forming a metal oxide film on the first electrode film, the metal oxide film including an upper surface provided with a first step; forming a second electrode film on the metal oxide film; forming a gas detecting element including a first electrode, a metal oxide layer, and a second electrode by patterning the first electrode film, the metal oxide film, and the second electrode film so as to include the first step as viewed in plan view; forming a first insulating film so as to cover the gas detecting element; and forming an opening by removing a part of the first insulating film, the opening allowing a part of the second electrode on the first step to be exposed therethrough as viewed in plan view.

The method of manufacturing a gas sensor according to one aspect of the present disclosure may further include: forming a second insulating film on the substrate; forming a first contact plug in the second insulating film; and removing an upper portion of the second insulating film surrounding the first contact plug so that an upper surface of the first contact plug projects from an upper surface of the second insulating film surrounding the first contact plug by. The first electrode film, the metal oxide film, and the second electrode film may be formed in this order on the first contact plug and the second insulating film so as to cross over a second step, and the gas detecting element including the first step resulting from a transfer of the second step may be formed. The second step may be a step between the upper surface of the first contact plug and the upper surface of the second insulating film surrounding the first contact plug.

The method of manufacturing a gas sensor according to one aspect of the present disclosure may further include: forming a second insulating film on the substrate; forming a first contact plug in the second insulating film; and removing an upper portion of the first contact plug so that an upper surface of the first contact plug is recessed from an upper surface of the second insulating film surrounding the first contact plug. The first electrode film, the metal oxide film, and the second electrode film may be formed in this order on the first contact plug and the second insulating film so as to cross over a third step, and the gas detecting element including the first step resulting from a transfer of the third step may be formed. The third step may be a step between the upper surface of the first contact plug and the upper surface of the second insulating film surrounding the first contact plug.

A fuel cell vehicle according to one aspect of the present disclosure includes a passenger compartment, a gas tank compartment housing a hydrogen gas tank, a fuel cell compartment housing a fuel cell, and the gas sensor according to any one of the above aspects. The gas sensor is provided in at least one of the gas tank compartment or the fuel cell compartment.

Hereinafter, some embodiments of the present disclosure will be described with reference to the drawings.

In the drawings, substantially identical configurations and operations and elements representing substantially identical effects are given identical reference characters, and duplicate descriptions thereof will be omitted. In addition, the numerical values, the materials, the deposition methods, and so on described below are all illustrative in nature and are merely for describing the embodiments of the present disclosure in concrete terms, and the present disclosure is not limited thereby. Moreover, the manners how the constituent elements are connected relative to each other in the following description are illustrative in nature and merely for describing the embodiments of the present disclosure in concrete terms, and how the constituent elements are connected relative to each other to implement the functions of the present disclosure is not limited thereto.

Embodiment 1

Configuration of Gas Sensor

A gas sensor according to Embodiment 1 is a gas sensor of a metal-insulator-metal (MIM) structure in which a metal oxide layer serving as an insulating film and metal films are laminated together. This gas sensor can detect, without being heated by a heater, a hydrogen-containing gas by utilizing the self-heat generation and the gas sensitivity in a local region formed within the metal oxide layer. In this example, the term "hydrogen-containing gas" is a collective term for gasses that include molecules containing hydrogen atoms, and examples of such hydrogen-containing gases can include hydrogen, methane, and alcohol.

FIG. 1A is a cross-sectional view illustrating an example of a configuration of gas sensor 100 according to the present embodiment.

Figure 1B:
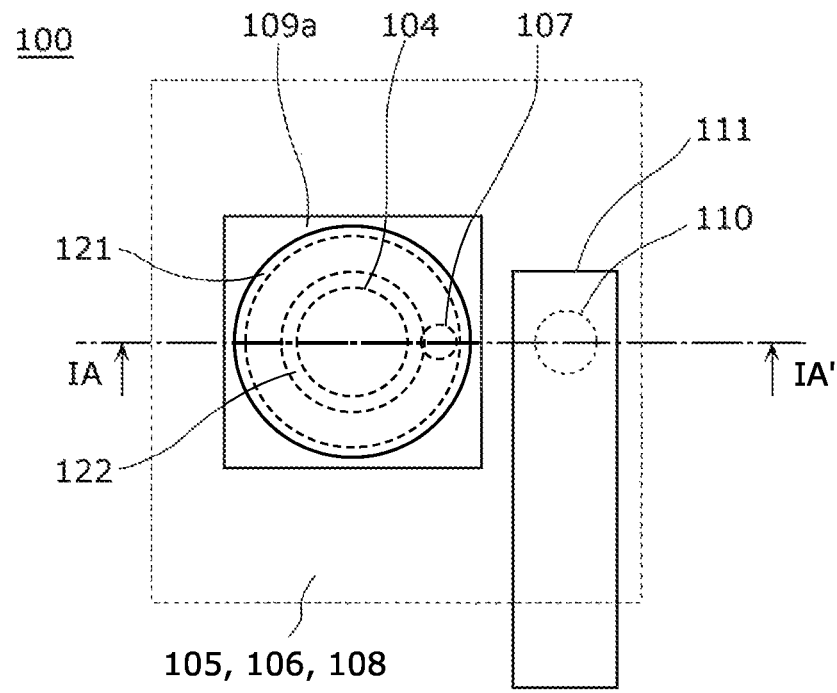
FIG. 1B is a plan view of the gas sensor according to Embodiment 1.

FIG. 1B is a top view illustrating an example of the configuration of gas sensor 100 according to the present embodiment.

The cross section illustrated in FIG. 1A corresponds to the cross section cut along the IA-IA' line indicated in FIG. 1B and viewed in the direction indicated by the arrows.

Gas sensor 100 includes substrate 101; first wiring 102; second insulating film 103 disposed on first wiring 102; first contact plug 104 penetrating through second insulating film 103 and connected to first wiring 102; first electrode 105, metal oxide layer 106, and second electrode 108 formed in this order from a lower side on second insulating film 103 so as to cover first contact plug 104; first insulating film 109 that covers at least a part of first electrode 105, a part of metal oxide layer 106, and a part of second electrode 108; second contact plug 110 penetrating through first insulating film 109 and connected to second electrode 108; and second wiring 111 formed on first insulating film 109 so as to connect to second contact plug 110.

In this example, an upper surface of first contact plug 104 lies higher than an upper surface of second insulating film 103, and second step 122 is formed by first contact plug 104 and second insulating film 103 adjacent to first contact plug 104.

As such, first step 121 is formed in first electrode 105, metal oxide layer 106, and second electrode 108 over first contact plug 104, as second step 122 formed by first contact plug 104 and second insulating film 103 adjacent to first contact plug 104 is transferred to first electrode 105, metal oxide layer 106, and second electrode 108.

Moreover, opening 109a is formed in first insulating film 109 over second electrode 108, and an upper surface of second electrode 108 is exposed through opening 109a.

In this example, as illustrated in FIG. 1B, first step 121 on second electrode 108 is exposed at the bottom of opening 109a, and first step 121 is formed as second step 122 formed by first contact plug 104 and second insulating film 103 adjacent to first contact plug 104 is transferred onto second electrode 108. First step 121 is of an upwardly convex shape. In this example, it is not essential that first step 121 be exposed on the upper surface of second electrode 108. It suffices that first step 121 be formed at a portion located within opening 109a, as viewed in plan view, at an interface between metal oxide layer 106 and second electrode 108.

Metal oxide layer 106 is a layer whose resistance value changes reversibly in accordance with an electrical signal given across first electrode 105 and second electrode 108. For example, metal oxide layer 106 transitions reversibly between a high-resistance state and a low-resistance state in accordance with the voltage applied across first electrode 105 and second electrode 108 and the presence or absence of a hydrogen-containing gas in a gas that comes into contact with second electrode 108.

Local region 107 is present inside metal oxide layer 106, and local region 107 is in contact with second electrode 108 but is not in contact with first electrode 105.

In this example, local region 107 is a small region that includes a filament formed of an oxygen vacant site, and the filament functions as an electrically conductive path.

To be more specific, metal oxide layer 106 is formed of a metal oxide, and the degree of oxygen deficiency of the metal oxide included in local region 107 of metal oxide layer 106 is greater than the degree of oxygen deficiency of the metal oxide included in a portion of metal oxide layer 106 other than local region 107.

The degree of oxygen deficiency of the metal oxide included in local region 107 changes reversibly in accordance with the voltage applied across first electrode 105 and second electrode 108 and the presence or absence of a hydrogen-containing gas in a gas that comes into contact with second electrode 108 via opening 109a.

The "degree of oxygen deficiency" as used in the present specification refers to, with regard to a metal oxide, the proportion of oxygen that is in deficit relative to the amount of oxygen to be contained in the oxide of a stoichiometric composition. When there are a plurality of stoichiometric compositions as the stoichiometric composition of a given metal oxide, the stoichiometric composition of a metal oxide in the present specification means a stoichiometric composition having the highest resistance value among the plurality of stoichiometric compositions.

A metal oxide of the stoichiometric composition is more stable and has a higher resistance value than metal oxides of other composition states outside the stoichiometric composition state.

For example, when a metal is tantalum (Ta), its oxide of the stoichiometric composition of the above definition is $Ta_2O_5$. $Ta_2O_5$ can also be expressed as $TaO_{2.5}$. The degree of oxygen deficiency of $TaO_{2.5}$ is 0%.

In one example, the degree of oxygen deficiency of $TaO_{1.5}$ is (2.5−1.5)/2.5=40%. In addition, the degree of oxygen deficiency of an oxygen-excess metal oxide takes a negative value. In the present specification, the degree of oxygen deficiency takes a positive value, 0, or a negative value, unless specifically indicated otherwise.

As such, a metal oxide with a low degree of oxygen deficiency is closer to a metal oxide of the stoichiometric composition and thus has a high resistance value, whereas a metal oxide with a high degree of oxygen deficiency is closer to the metal that is the constituent element of the metal oxide and thus has a low resistance value.

The term "oxygen content by percentage" means the proportion of oxygen atoms with respect to the total number of atoms. For example, the oxygen content by percentage of $Ta_2O_5$ is the proportion of the oxygen atoms with respect to the total number of atoms (O/(Ta+O)), which is 71.4 atm %. Accordingly, the oxygen content by percentage of a tantalum oxide of an oxygen deficit type is greater than 0 and smaller than 71.4 atm %.

Herein, local region 107 is formed in metal oxide layer 106 as an initial breakdown voltage is applied across first electrode 105 and second electrode 108. The initial breakdown voltage may be a voltage having a higher absolute value than a normal write voltage applied across first electrode 105 and second electrode 108 so as to cause metal oxide layer 106 to transition reversibly between the high-resistance state and the low-resistance state or may be a voltage having a smaller absolute value than such a write voltage. Moreover, the initial breakdown voltage may be applied repeatedly or applied continuously for a predetermined time.

As the initial breakdown voltage is applied, local region 107 that is in contact with second electrode 108 but is not in contact with first electrode 105 is formed within metal oxide layer 106, as illustrated in FIG. 1A.

In this example, local region 107 is produced so as to be concentrated in a portion near first step 121 on metal oxide layer 106, where first step 121 is formed as second step 122 formed between first contact plug 104 and second insulating film 103 is transferred onto metal oxide layer 106.

This is because when the initial breakdown voltage is applied across first electrode 105 and second electrode 108, the electric field is enhanced near first step 121 on metal oxide layer 106 and thus local region 107 is formed more easily particularly in the region near first step 121.

It is conceivable that local region 107 includes a filament formed of an oxygen vacant site. Moreover, the size of local region 107 is small so as to be in balance with the filament required to pass the current therethrough. Formation of the filament in local region 107 is described by use of a percolation model.

A percolation model is a model that is based on a theory stating that, with the assumption that oxygen vacant sites (simply referred to below as vacant sites) are distributed randomly within local region 107, the probability that a link between the vacant sites is formed increases when the density of the vacant sites has exceeded a threshold.

According to the percolation model, the filament is formed as a plurality of vacant sites within local region 107 are linked together. Moreover, according to the percolation model, the change in the resistance in metal oxide layer 106 appears due to an occurrence and a disappearance of a vacant site in local region 107.

In this example, the term "vacant" or "vacancy" means that a metal oxide lacks oxygen from its stoichiometric composition. The expression "the density of vacant sites" corresponds to the degree of oxygen deficiency. In other words, as the degree of oxygen deficiency increases, so does the density of vacant sites.

Local region 107 may be formed only at one location in metal oxide layer 106 of gas sensor 100. The number of local regions 107 in metal oxide layer 106 can be checked through, for example, an electron beam absorbed current (EBAC) analysis.

As local region 107 is formed in metal oxide layer 106, the current in metal oxide layer 106 flows concentratedly to local region 107 when the voltage is applied across first electrode 105 and second electrode 108. Since local region 107 is small, the temperature rises considerably through heat generated by the current of several tens of μA (i.e., power consumption of less than 0.1 mW) caused when a voltage of around 1 V is applied to read out the resistance value, for example.

As such, second electrode 108 is formed of a metal having a catalytic effect or formed, for example, of platinum, and the region of second electrode 208 where second electrode 208 makes contact with local region 107 is heated by heat generated in local region 107. This can increase the efficiency of dissociating a hydrogen-containing gas to yield hydrogen atoms. As a result, when there is a hydrogen-containing gas in a gas to be inspected, the hydrogen atoms resulting from the hydrogen-containing gas dissociated by second electrode 108 couple with oxygen atoms within local region 107, and thus the resistance value of local region 107 decreases.

Gas sensor 100 has a characteristic in which the resistance value of metal oxide layer 106 decreases when second electrode 108 comes into contact with a hydrogen-containing gas through the mechanism described above. With this characteristic, a hydrogen-containing gas included in a gas to be inspected can be detected by bringing the gas to be inspected into contact with second electrode 108 and observing the decrease in the resistance value across first electrode 105 and second electrode 108.

Regardless of whether local region 107 is in the high-resistance state or the low-resistance state, the resistance value further decreases as a hydrogen-containing gas comes into contact with second electrode 108. Therefore, a hydrogen-containing gas can be detected by the gas sensor regardless of whether local region 107 is in the high-resistance state or the low-resistance state. However, in order to detect a decrease in the resistance value more clearly, a gas sensor in which local region 107 is set to an electrically high-resistance state in advance may be used.

In the following section, the details of gas sensor 100 for obtaining a stable resistance change characteristic will be described.

An assumption here is that metal oxide layer 106 contains a metal oxide of an oxygen deficit type. For the base metal of the metal oxide, at least one metal may be selected from the group consisting of transition metals such as tantalum, hafnium (Hf), titanium (Ti), zirconium (Zr), niobium (Nb), tungsten (W), nickel (Ni), and iron (Fe) and aluminum (Al). In particular, since transition metals can take a plurality of oxidation states, different resistance states can be achieved through the oxidation-reduction reaction.

In this example, a metal oxide of an oxygen deficit type refers to a metal oxide with an oxygen content (atomic ratio) smaller than that of the composition of the metal oxide having the stoichiometric composition that is normally an insulator. Many metal oxides of an oxygen deficit type behave like a semiconductor in a normal state. The use of a metal oxide of an oxygen deficit type as metal oxide layer 106 makes it possible to achieve a highly reproducible and stable resistance changing operation in gas sensor 100.

For example, when hafnium oxide is used as the metal oxide contained in metal oxide layer 106, if x is 1.6 or greater when the composition of the hafnium oxide is expressed as $HfO_x$, the resistance value of metal oxide layer 106 can be changed stably. In this case, the hafnium oxide may have a film thickness of 3 nm to 4 nm.

Meanwhile, when zirconium oxide is used as the metal oxide contained in metal oxide layer 106, if x is 1.4 or greater when the composition of the hafnium oxide is expressed as $ZrO_x$, the resistance value of metal oxide layer 106 can be changed stably. In this case, the zirconium oxide may have a film thickness of 1 nm to 5 nm.

Meanwhile, when tantalum oxide is used as the metal oxide contained in metal oxide layer 106, if x is 2.1 or greater when the composition of the hafnium oxide is expressed as $TaO_x$, the resistance value of metal oxide layer 106 can be changed stably.

The compositions of the metal oxide layers illustrated above can be measured by use of the Rutherford backscattering spectrometry.

Materials for first electrode 105 and second electrode 108 may be selected, for example, from platinum, iridium (Ir), palladium (Pd), silver (Ag), nickel, tungsten, copper (Cu), aluminum, tantalum, titanium, titanium nitride (TiN), tantalum nitride (TaN), and titanium aluminum nitride (TiAlN).

Specifically, for the material for second electrode 108, a material having a catalytic effect of dissociating a gas molecule containing hydrogen atoms into the hydrogen atoms may be used, and examples of such a material may include platinum, iridium, and palladium. Meanwhile, for the material for first electrode 105, a material having a standard electrode potential lower than that of the metal constituting the metal oxide may be used, and examples of such a material may include tungsten, nickel, tantalum, titanium, aluminum, tantalum nitride, and titanium nitride. In this example, as the standard electrode potential is higher, the material is oxidized less easily.

For substrate 101, a silicon single crystal substrate or a semiconductor substrate, for example, can be used, but these are not limiting examples. Metal oxide layer 106 can be formed at a relatively low substrate temperature, and therefore metal oxide layer 106 can be formed even on a resin material or the like, for example.

Moreover, gas sensor 100 may further include, for example, a fixed resistance, a transistor, or a diode as a load element electrically connected to metal oxide layer 106.

Moreover, gas sensor 100 may include a measuring circuit that measures the current that flows in metal oxide layer 106 when a predetermined voltage is applied across first electrode 105 and second electrode 108. Alternatively, gas sensor 100 may include a power supply circuit that applies a predetermined voltage continuously across first electrode 105 and second electrode 108. With such a configuration, a highly utilizable gas sensor can be obtained as a module component including a measuring circuit or a power supply circuit.

Method of Manufacturing Gas Sensor

In the following section, an example of a method of manufacturing gas sensor 100 according to the present embodiment will be described with reference to FIGS. 2A to 2J, FIG. 3, and FIG. 4.

Figure 2A:
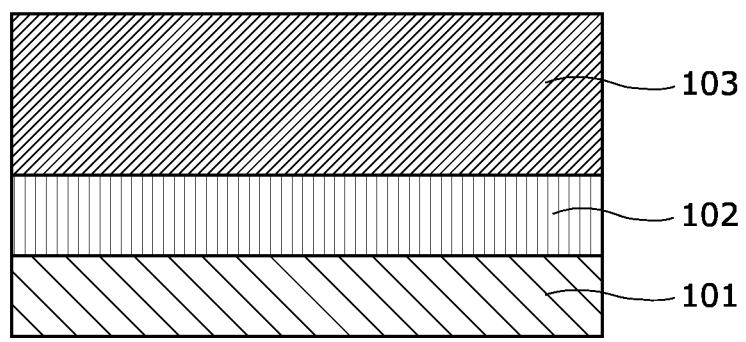
FIG. 2A is a cross-sectional view illustrating a method of manufacturing the gas sensor according to Embodiment 1.

First, as illustrated in FIG. 2A, aluminum is deposited, for example, on silicon substrate 101 to the thickness of, for example, 400 nm. Then, a wiring pattern is patterned through a photolithography technique, the aluminum is etched through a dry etching technique, and the aluminum is processed into a wiring pattern to form first wiring 102. At this point, an insulating film formed, for example, through a chemical vapor deposition (CVD) technique may be interposed between first wiring 102 and silicon substrate 101. First wiring 102 can also be formed of copper, instead of aluminum, or an adhesive layer made of titanium, titanium nitride, or the like, may also be formed on top of and under the aluminum.

Then, a silicon oxide film is deposited on first wiring 102 through, for example, a CVD technique, to the thickness of 500 nm to form second insulating film 103. In this case, second insulating film 103 may have a layered structure of a silicon oxide film and a silicon nitride film.

Figure 2B:
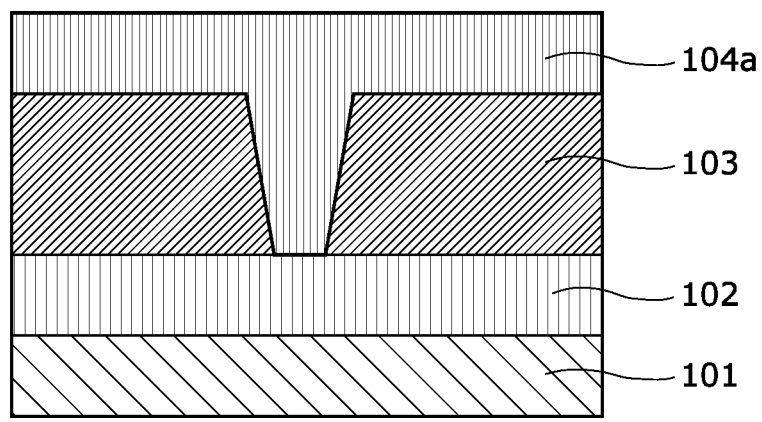
FIG. 2B is another cross-sectional view illustrating the method of manufacturing the gas sensor according to Embodiment 1.

Next, a mask patterned into a hole shape is disposed on second insulating film 103 through a photolithography technique, and then a hole penetrating through second insulating film 103 and reaching first wiring 102 is formed by use of the stated mask through a dry etching technique (not illustrated). Thereafter, as illustrated in FIG. 2B, tungsten is deposited on the entire surface of the wafer to the thickness of 800 nm through a CVD technique, and first contact plug film 104a is deposited within the hole so as to be in contact with first wiring 102. First contact plug film 104a may be made of copper, or an adhesive layer and a barrier layer made of titanium, titanium nitride, tantalum, tantalum nitride, or the like can be formed between first contact plug film 104a made of tungsten, copper, or the like and first wiring 102 and second insulating film 103.

Figure 2C:
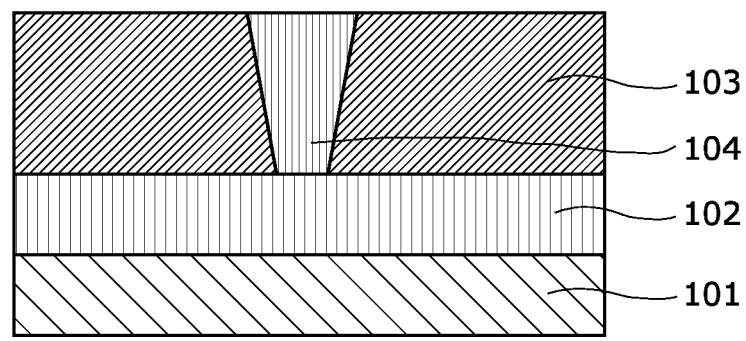
FIG. 2C is another cross-sectional view illustrating the method of manufacturing the gas sensor according to Embodiment 1.

Next, as illustrated in FIG. 2C, first contact plug film 104a is polished through a chemical mechanical polishing (CMP) technique to expose second insulating film 103, and first contact plug 104 is formed inside the hole.

The surface of first contact plug film 104a is set to be at least level with or lower than the surface of surrounding second insulating film 103.

Figure 2D:
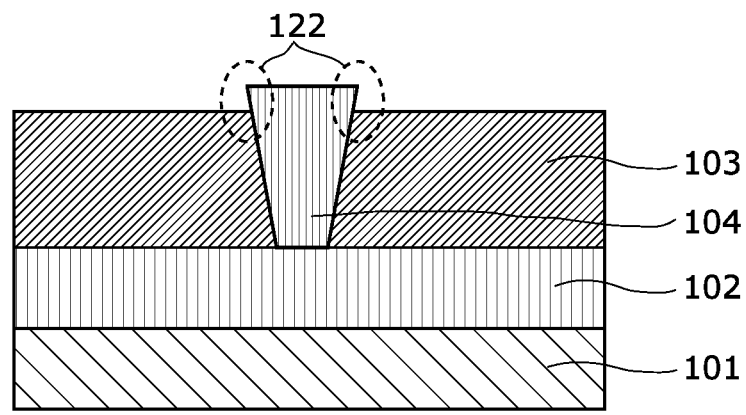
FIG. 2D is another cross-sectional view illustrating the method of manufacturing the gas sensor according to Embodiment 1.

Next, as illustrated in FIG. 2D, the upper portion of second insulating film 103 is etched, for example, by 50 nm with a chemical liquid containing hydrofluoric acid (HF) through a wet etching technique to allow the surface of the upper portion of first contact plug 104 to project from the surface of second insulating film 103 surrounding first contact plug 104. In this manner, second step 122 is formed at the border between first contact plug 104 and second insulating film 103.

Figure 2E:
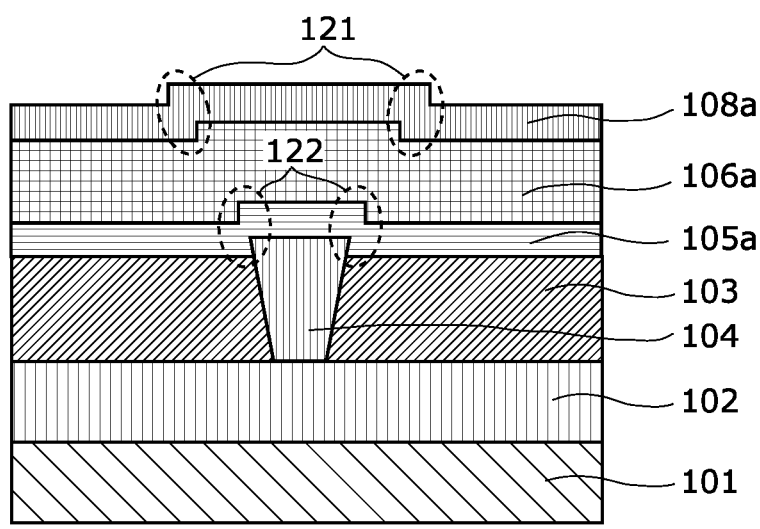
FIG. 2E is another cross-sectional view illustrating the method of manufacturing the gas sensor according to Embodiment 1.

Next, as illustrated in FIG. 2E, as first electrode film 105a, a tantalum nitride film having a thickness of, for example, 30 nm is formed so as to cover the surface of second insulating film 103 and the surface of first contact plug 104 projecting from the surface of second insulating film 103 through a sputtering technique. At this point, first electrode film 105a may be a laminated film of titanium, titanium nitride, or the like. Next, metal oxide film 106a having a thickness of 30 nm is formed on first electrode film 105a through a reactive sputtering technique in which, for example, Ta is used as a target. Next, as second electrode film 108a, a platinum film having a thickness of, for example, 10 nm is formed on metal oxide film 106a through a sputtering technique. In this example, the film thickness of the platinum film is desirably no less than 5 nm nor greater than 200 nm.

Through the above processes, second step 122 between the surface of second insulating film 103 and the surface of first contact plug 104 that is formed so as to project upward from the surface of surrounding second insulating film 103 is transferred to first electrode film 105a, metal oxide film 106a, and second electrode film 108a, and this results in a structure having first step 121 formed on second electrode film 108a near the border region between first contact plug 104 and second insulating film 103.

Figure 2F:
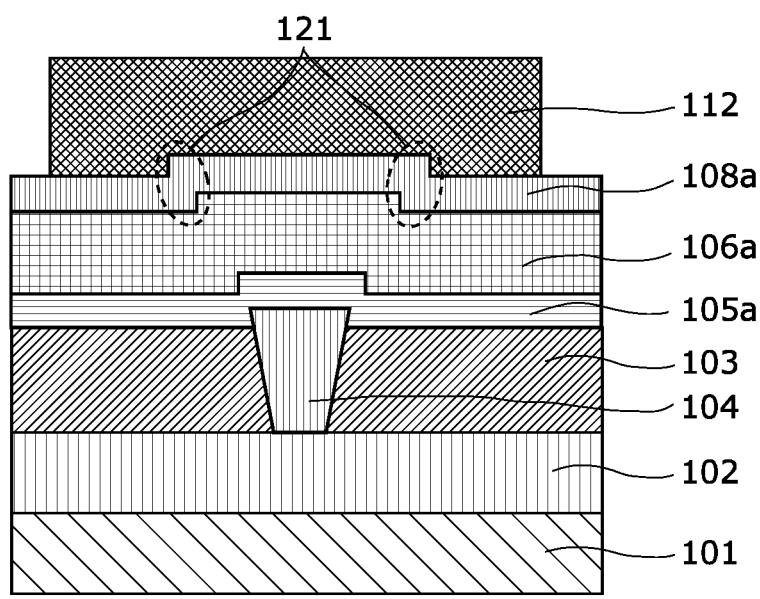
FIG. 2F is another cross-sectional view illustrating the method of manufacturing the gas sensor according to Embodiment 1.

Next, as illustrated in FIG. 2F, through, for example, a photolithography technique, first mask 112 composed of photoresist is formed into the shape of the sensor on second electrode film 108a that includes first step 121 as viewed in plan view. The dimensions of first mask 112 formed at this point as viewed in plan view may be, for example, from 1 μm on each side to 8 μm on each side.

Figure 2G:
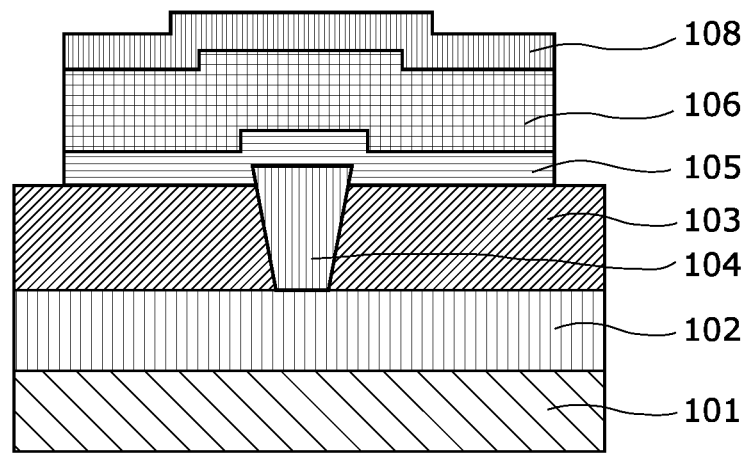
FIG. 2G is another cross-sectional view illustrating the method of manufacturing the gas sensor according to Embodiment 1.

Next, as illustrated in FIG. 2G, first electrode film 105a, metal oxide film 106a, and second electrode film 108a are patterned into the shape of the gas detecting element through a dry etching technique in which first mask 112 is used, and thus the gas detecting element including first electrode 105, metal oxide layer 106, and second electrode 108 is formed.

Figure 2H:
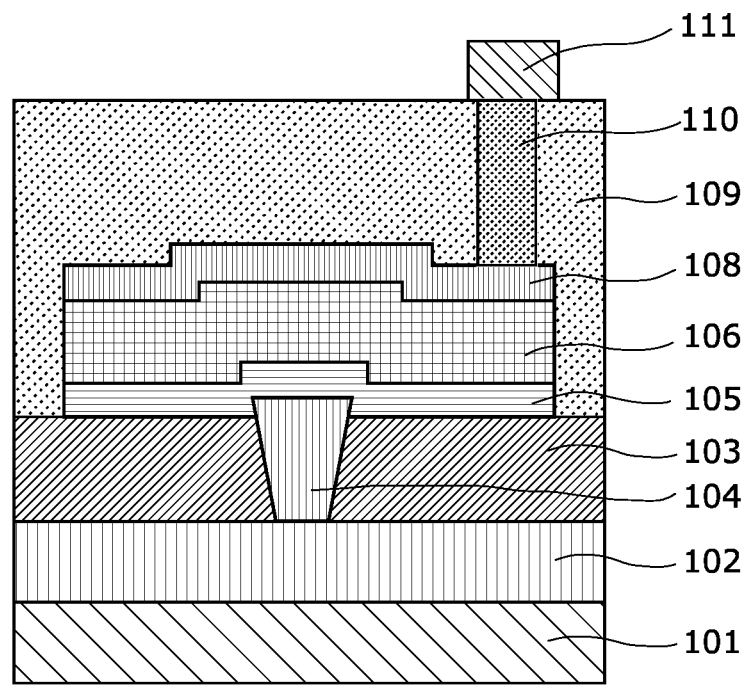
FIG. 2H is another cross-sectional view illustrating the method of manufacturing the gas sensor according to Embodiment 1.

Next, as illustrated in FIG. 2H, as first insulating film 109, a silicon oxide film having a thickness of, for example, 800 nm is formed so as to cover at least a part of metal oxide layer 106 and a part of second electrode 108. Thereafter, the upper portion of first insulating film 109 is polished by 300 nm through a CMP technique to flatten the surface of first insulating film 109. Thereafter, a via hole penetrating through first insulating film 109 and reaching a part of second electrode 108 is formed through an etching technique, tungsten is deposited on the entire surface of the wafer to the thickness of 800 nm through a CVD technique, and then the tungsten is flattened so as to remain only inside the plug through a CMP technique. Thus, second contact plug 110 is formed. Thereafter, another conductive film is deposited on first insulating film 109 and patterned, and thus second wiring 111 connected to second contact plug 110 is formed.

Figure 2I:
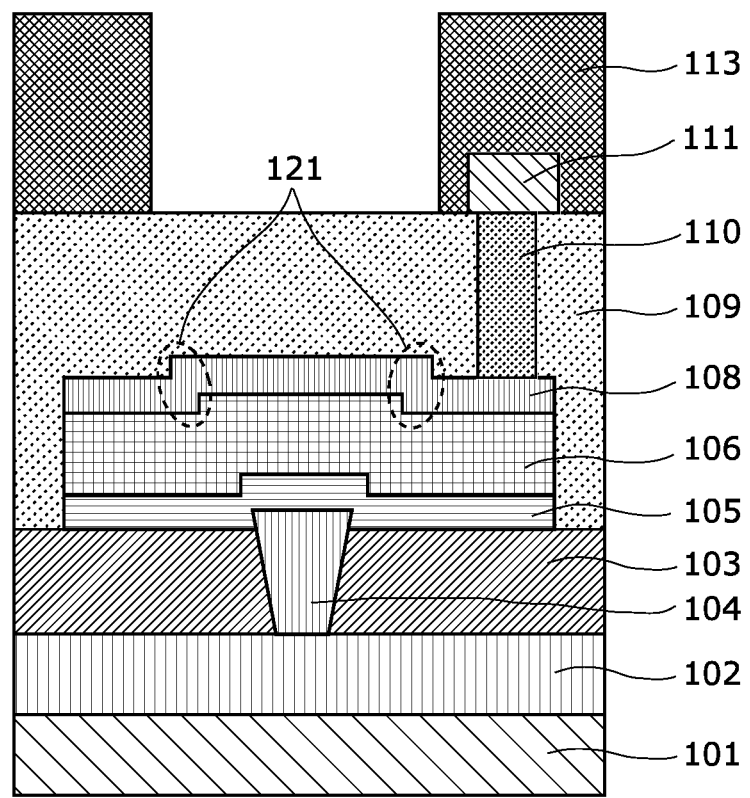
FIG. 2I is another cross-sectional view illustrating the method of manufacturing the gas sensor according to Embodiment 1.

Next, as illustrated in FIG. 2I, second mask 113 composed of photoresist is formed on first insulating film 109 through a lithography technique. At this point, as viewed in plan view, the opening in second mask 113 is formed into a shape that includes the entirety of first step 121 formed on second electrode 108 within second electrode 108.

Figure 2J:
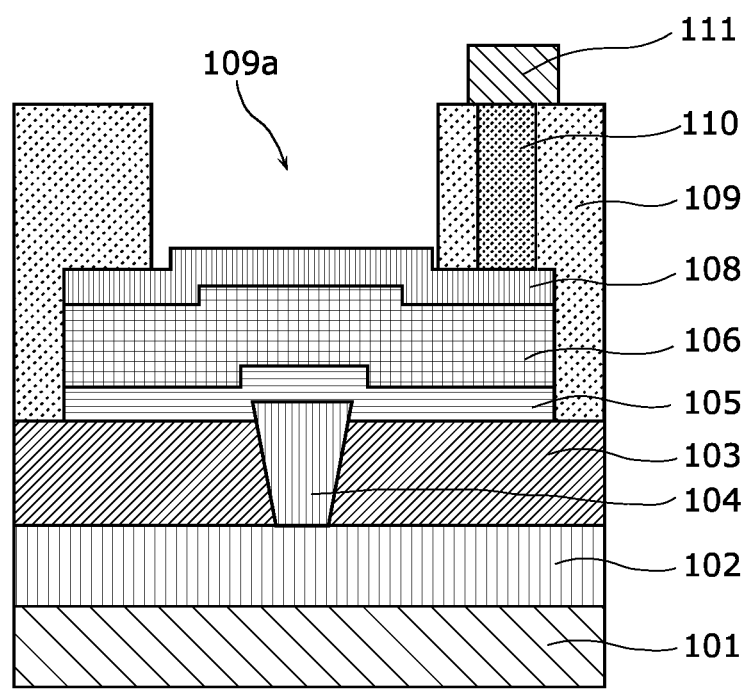
FIG. 2J is another cross-sectional view illustrating the method of manufacturing the gas sensor according to Embodiment 1.

Next, as illustrated in FIG. 2J, first insulating film 109 is etched by use of second mask 113 through a dry etching technique, and opening 109a exposing a part of the surface of second electrode 108 is formed.

Figure 3:
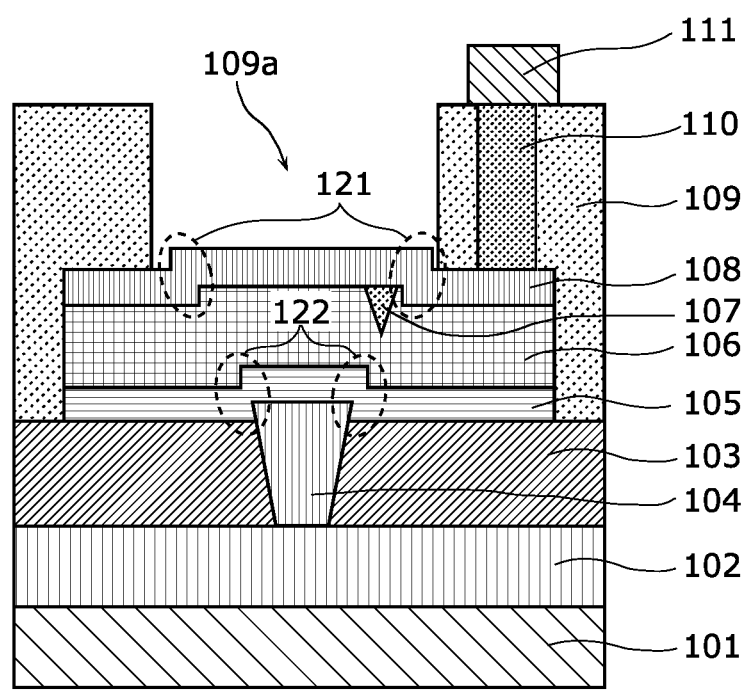
FIG. 3 is a cross-sectional view of the gas sensor according to Embodiment 1.

Next, as illustrated in FIG. 3, an initial breakdown voltage is applied across first electrode 105 and second electrode 108 in gas sensor 100 to form local region 107 within metal oxide layer 106, and thus gas sensor 100 is completed.

As described above, local region 107 is generated concentratedly in metal oxide layer 106 near first step 121 formed as second step 122 formed between first contact plug 104 and second insulating film 103 is transferred onto metal oxide layer 106. Specifically, local region 107 is generated concentratedly near first step 121 formed on second electrode 108.

Hydrogen-Containing Gas Reaction Characteristics

First, with regard to one example of the resistance change characteristic associated with the voltage application in gas sensor 100 according to the present embodiment, a result of a measurement by a sample element will be described. The resistance change characteristic of gas sensor 100 caused by a hydrogen-containing gas according to the present embodiment will be described later.

Figure 4:
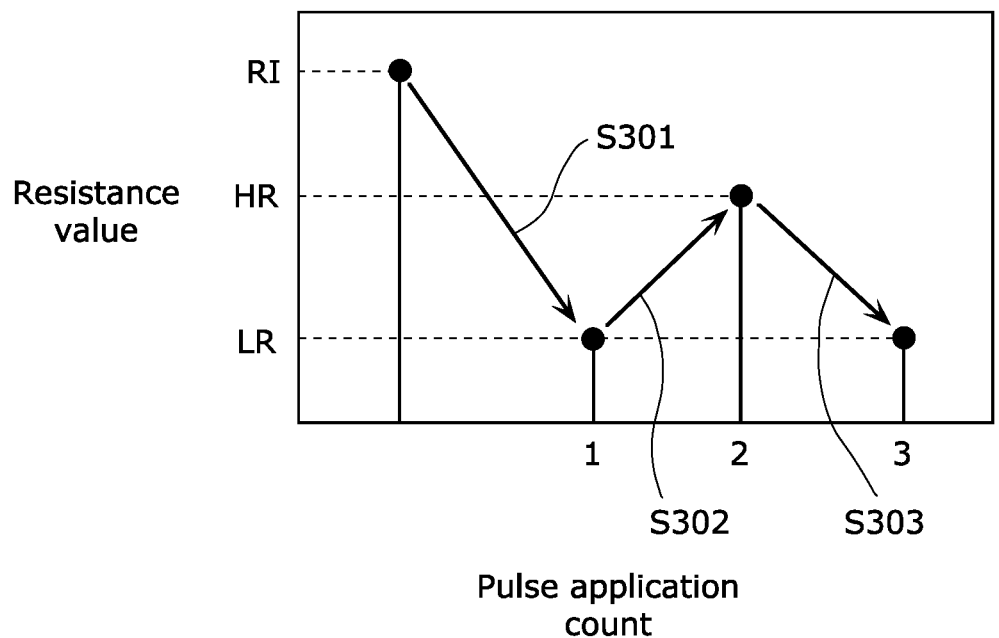
FIG. 4 illustrates a method of forming a local region in the gas sensor according to Embodiment 1.

FIG. 4 illustrates a measurement result indicating an example of the resistance change characteristic of gas sensor 100 caused by the voltage application according to the present embodiment.

In gas sensor 100 serving as a sample element, first electrode 105, second electrode 108, and metal oxide layer 106 each have dimensions of 3 μm by 3 μm (the area of 9 μm$^2$). When the composition of the tantalum oxide contained in metal oxide layer 106 is expressed as TaO$_y$, y is set to 2.47, and the thickness of metal oxide layer 106 is set to 5 nm.

When a read voltage (e.g., 0.4 V) is applied across first electrode 105 and second electrode 108 in gas sensor 100 configured as described above, initial resistance value RI is from about $10^6 \Omega$ to $10^9 \Omega$.

As illustrated in FIG. 4, when the resistance value of gas sensor 100 is at initial resistance value RI that is higher than resistance value HR in the high-resistance state, applying the initial breakdown voltage (e.g., 3 V) across first electrode 105 and second electrode 108 causes the resistance value to change to low resistance value LR (step S301).

Next, when two types of voltage pulses, for example, having a pulse duration of 100 ns and having different polarities, or specifically, a positive voltage pulse (e.g., 2.5 V) and a negative voltage pulse (e.g., 1.8 V), are applied as write voltages in an alternating manner across first electrode 105 and second electrode 108 of gas sensor 100, the resistance value of metal oxide layer 106 changes, as illustrated in FIG. 4.

In other words, when a positive voltage pulse is applied across the electrodes as a write voltage, the resistance value of metal oxide layer 106 increases from low resistance value LR to high resistance value HR (step S302). Meanwhile, when a negative voltage pulse is applied across the electrodes as a write voltage, the resistance value of metal oxide layer 106 decreases from high resistance value HR to low resistance value LR (step S303). The polarity of the voltage pulse is defined as being positive when the potential of second electrode 108 is higher than the potential of first electrode 105 or defined as being negative when the potential of second electrode 108 is lower than the potential of first electrode 105.

Utilizing such a resistance change characteristic caused by the voltage application, gas sensor 100 is set to be in the high-resistance state by applying a positive voltage pulse in the end across first electrode 105 and second electrode 108 before starting to monitor a hydrogen-containing gas.

With this initial setting, as described above, any decrease in the resistance value can be detected more clearly than in a case where a hydrogen-containing gas is detected by use of gas sensor 100 in the low-resistance state, and thus the performance of detecting a hydrogen-containing gas improves.

Next, the resistance change characteristic of gas sensor 100 caused by a hydrogen-containing gas according to the present embodiment will be described.

Figure 5:
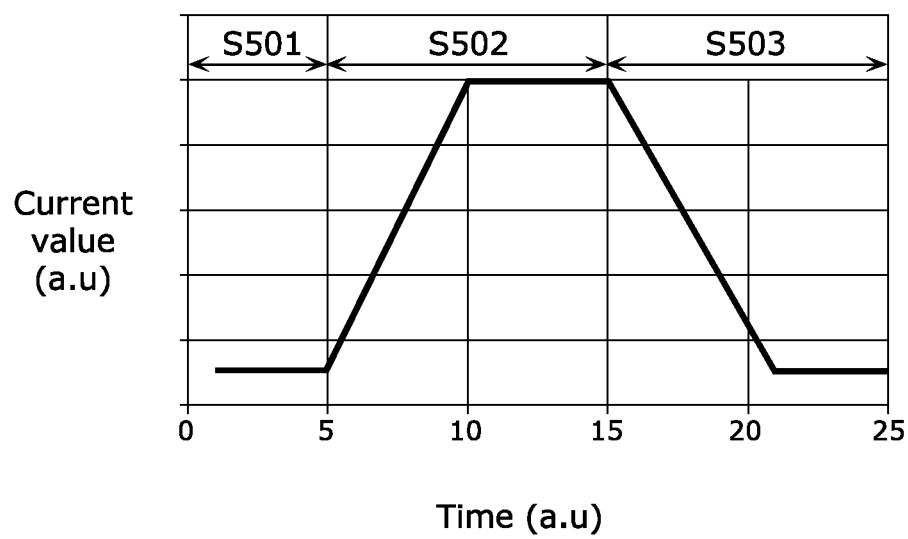
FIG. 5 is a graph illustrating a result of evaluating the gas sensor according to Embodiment 1.

FIG. 5 is a graph illustrating an example of evaluating gas sensor 100 according to the present embodiment. The horizontal axis represents the time (a.u.), and the vertical axis represents the current value (a.u.) of the current that flows between first electrode 105 and second electrode 108.

In the experiment, first, a nitrogen gas was introduced into a closed vessel housing gas sensor 100. Then, the nitrogen gas was switched to a hydrogen gas, and the hydrogen gas was then switched to a nitrogen gas. Gas sensor 100 in which local region 107 was set to the high-resistance state in advance by applying a predetermined voltage across first electrode 105 and second electrode 108 was used.

FIG. 5 illustrates the evaluation result obtained in this experiment, and the horizontal axis indicates three periods: the initial introduction of nitrogen (step S501), the introduction of hydrogen (step S502), and the subsequent introduction of nitrogen (step S503). FIG. 5 reveals that the current value started increasing immediately after the introduced gas was switched from a nitrogen gas to a hydrogen gas. Moreover, FIG. 5 reveals that the current started decreasing immediately after the introduced gas was switched from a hydrogen gas to a nitrogen gas.

In a specific operation of monitoring a hydrogen-containing gas, while a detection voltage of 0.6 V was applied across first electrode 105 and second electrode 108, a current of from 10 µA to 20 µA flowed between first electrode 105 and second electrode 108 when the hydrogen gas was detected. In other words, the experiment reveals that, with gas sensor 100 according to the present embodiment, a hydrogen-containing gas can be monitored with very small power consumption of from 0.006 mW to 0.012 mW.

Based on this result, the inventors speculate as follows concerning the mechanism of detecting a hydrogen gas with gas sensor 100.

First, when a hydrogen-containing gas comes into contact with second electrode 108, the hydrogen-containing gas is dissociated to yield hydrogen atoms through the catalytic effect of second electrode 108. The resulting hydrogen atoms diffuse within second electrode 108 so as to maintain the state of equilibrium and reach local region 107.

Next, these hydrogen atoms cause a reductive reaction of the metal oxide in local region 107, and as oxygen in local region 107 bonds with hydrogen, the degree of oxygen deficiency of the metal oxide included in local region 107 increases. As a result, filaments in local region 107 link together more easily, and the resistance value of local region 107 decreases. Thus, the current that flows between first electrode 105 and second electrode 108 increases.

In contrast, when the hydrogen-containing gas ceases to exist near second electrode 108, hydrogen atoms turn into hydrogen molecules near the surface of second electrode 108 so as to maintain the state of equilibrium and thus move to the outer side from the surface of second electrode 108.

As such, a reaction in which water molecules generated in local region 107 through the previous reductive reaction are decomposed into hydrogen atoms and oxygen atoms occurs, and the hydrogen atoms generated in local region 107 return into second electrode 108. Meanwhile, the oxygen atoms generated in local region 107 bond with oxygen vacancies, and thus the degree of oxygen deficiency of the metal oxide included in local region 107 decreases. As a result, filaments in local region 107 become harder to link together, and the resistance value increases. Thus, the current that flows between first electrode 105 and second electrode 108 decreases.

The operation described above is not limited to gas sensor 100 according to the present embodiment and is considered to occur in a similar manner in a gas sensor of which the structure of the pertinent portions is substantially equal to that of gas sensor 100 according to the present embodiment or in other gas sensors described later.

The operation described above is not limited to a case where the gas that comes into contact with second electrode 108 is a hydrogen gas and is considered to occur in a similar manner even in a case where, for example, the gas that comes into contact with second electrode 108 is a hydrogen-containing gas, such as methane or alcohol.

Next, some advantageous effects of the step formed by first contact plug 104 and second insulating film 103 will be described.

Figure 6:
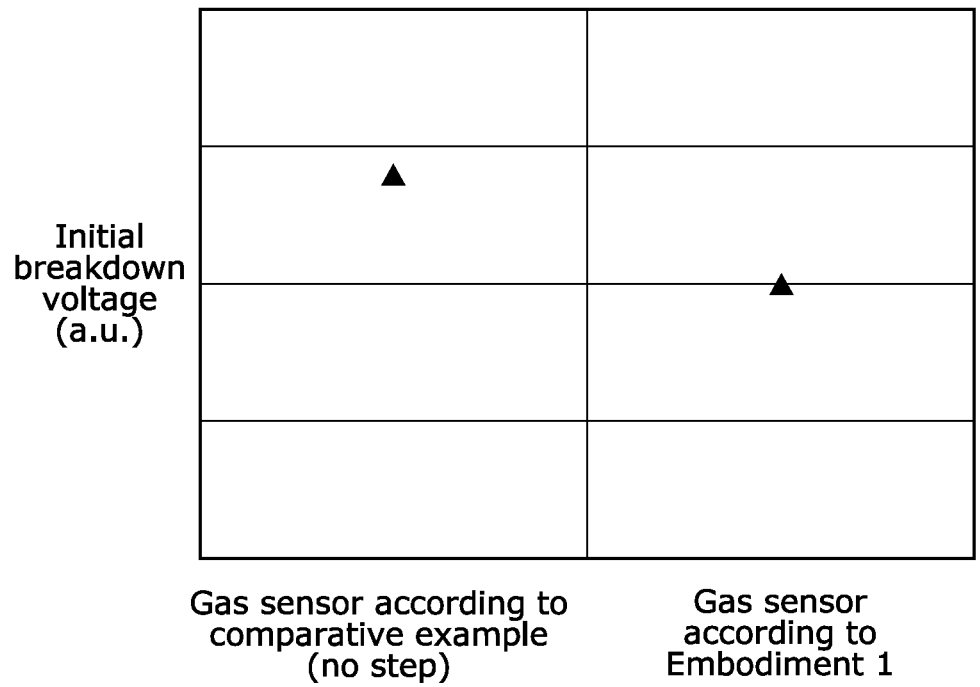
FIG. 6 illustrates a result of evaluating a no-step gas sensor and the gas sensor according to Embodiment 1.

FIG. 6 illustrates a result of comparing the initial breakdown voltage of metal oxide layer 106 between a gas sensor according to a comparative example that is formed through a method similar to that for the gas sensor according to the present embodiment except that no step is formed (referred to below as a no-step gas sensor) and a gas sensor formed according to the present embodiment.

As can be seen clearly from FIG. 6, the initial breakdown voltage is lower in the gas sensor according to the present embodiment. This is due to the following. The step shape formed on first contact plug 104 and second insulating film 103 is transferred to first electrode 105, metal oxide layer 106, and second electrode 108 as well, and thus the electric field is enhanced at this step portion, which causes the effective voltage applied to metal oxide layer 106 to rise. Therefore, local region 107 is formed selectively near the step portion.

Figure 7:
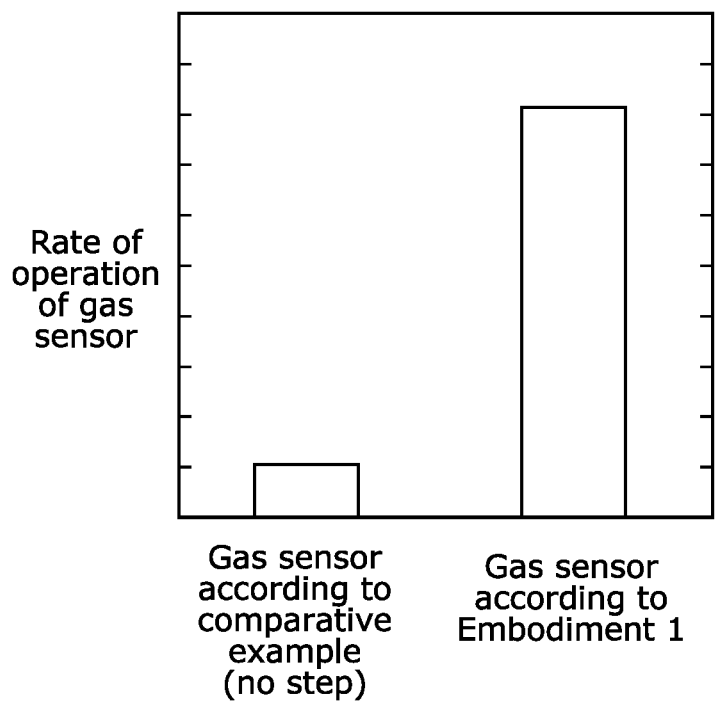
FIG. 7 illustrates another result of evaluating the no-step gas sensor and the gas sensor according to Embodiment 1.

FIG. 7 illustrates the rate of operation of each of the no-step gas sensor and the gas sensor formed according to the present embodiment under the condition in which the concentration of hydrogen in the gas to be detected is, for example, 1%.

As can be seen clearly from FIG. 7, the rate of operation of the gas sensor formed according to the present embodiment improves more than the rate of operation of the no-step gas sensor. This is possibly because, since there is no step in the no-step gas sensor, local region 107 is formed randomly in the no-step gas sensor and can be formed at a location that is covered by first insulating film 109, for example. In this case, hydrogen may not reach local region 107, preventing the gas sensor from operating as a gas sensor. Meanwhile, in the gas sensor formed according to the present embodiment, it is highly likely that local region 107 is selectively formed at the step portion near first contact plug 104, and opening 109a is always formed so as to include the portion directly above first contact plug 104. Therefore, hydrogen can reach local region 107 via second electrode 108, and this causes the rate of operation as a gas sensor to improve.

As described thus far, with gas sensor 100 according to the present embodiment, gas sensor 100 does not need to be heated by a heater separately, and a hydrogen-containing gas can be detected stably. Thus, a gas sensor that excels in the power saving performance can be obtained.

Embodiment 2

Configuration of Gas Sensor

As with the gas sensor according to Embodiment 1 described above, a gas sensor according to Embodiment 2 is a gas sensor of a metal-insulator-metal (MIM) structure in which a metal oxide layer serving as an insulating film and metal films are laminated together. This gas sensor can detect, without being heated by a heater, a hydrogen-containing gas by utilizing the self-heat generation and the gas sensitivity in a local region formed within a gas sensitive resistance film. In this example, the term "hydrogen-containing gas" is a collective term for gasses that include molecules containing hydrogen atoms, and examples of such hydrogen-containing gases can include hydrogen, methane, and alcohol.

Figure 8A:
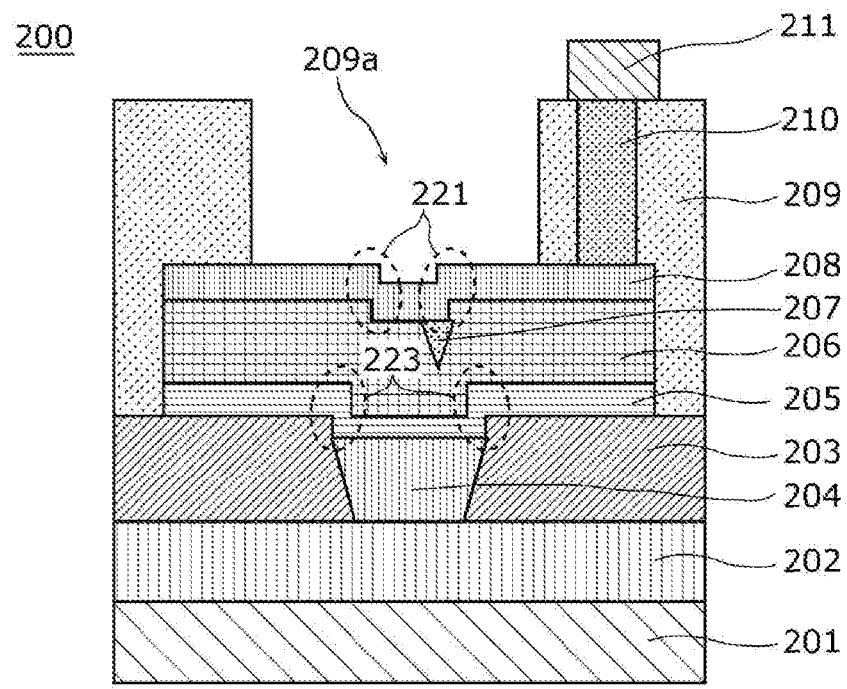
FIG. 8A is a cross-sectional view of a gas sensor according to Embodiment 2.

FIG. 8A is a cross-sectional view illustrating an example of a configuration of gas sensor 200 according to the present embodiment.

Figure 8B:
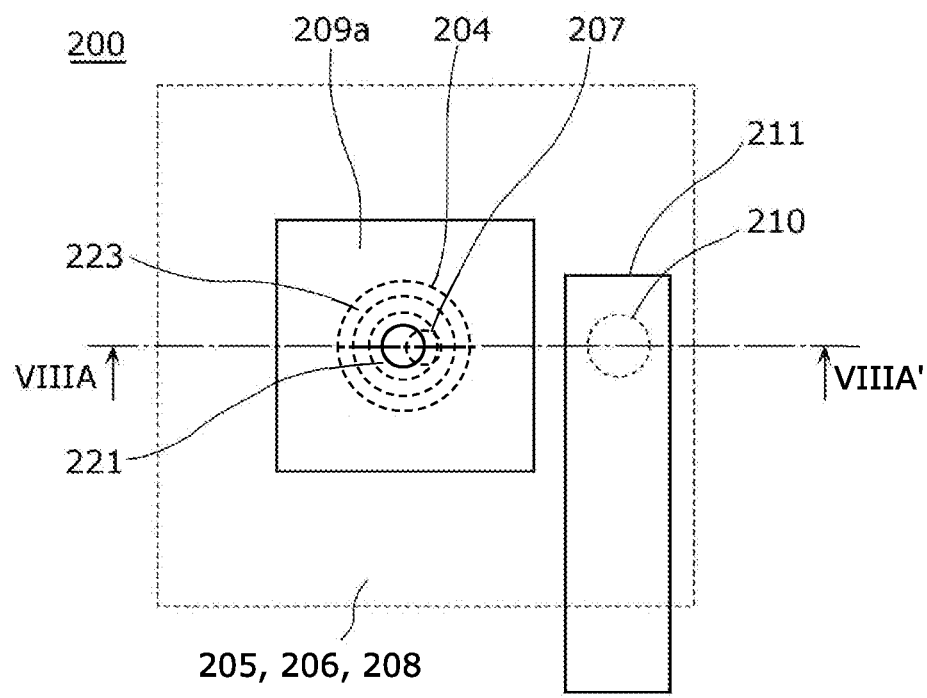
FIG. 8B is a plan view of the gas sensor according to Embodiment 2.

FIG. 8B is a top view illustrating an example of the configuration of gas sensor 200 according to the present embodiment.

The cross section illustrated in FIG. 8A corresponds to the cross section cut along the VIIIA-VIIIA' line indicated in FIG. 8B and viewed in the direction indicated by the arrows.

Gas sensor 200 includes substrate 201; first wiring 202; second insulating film 203 disposed on first wiring 202; first contact plug 204 penetrating through second insulating film 203 and connected to first wiring 202; first electrode 205, metal oxide layer 206, and second electrode 208 formed in this order from a lower side on second insulating film 203 so as to cover first contact plug 204; first insulating film 209 that covers at least a part of first electrode 205, a part of metal oxide layer 206, and a part of second electrode 208; second contact plug 210 penetrating through first insulating film 209 and connected to second electrode 208; and second wiring 211 formed on first insulating film 209 so as to connect to second contact plug 210.

In this example, an upper surface of first contact plug 204 lies lower than an upper surface of second insulating film 203, and third step 223 is formed by first contact plug 204 and second insulating film 203 adjacent to first contact plug 204.

As such, first step 221 is formed in first electrode 205, metal oxide layer 206, and second electrode 208 over first contact plug 204, as third step 223 formed by first contact plug 204 and second insulating film 203 adjacent to first contact plug 204 is transferred onto first electrode 205, metal oxide layer 206, and second electrode 208.

Moreover, opening 209a is formed in first insulating film 209 over second electrode 208, and an upper surface of second electrode 208 is exposed through opening 209a.

In this example, as illustrated in FIG. 8B, first step 221 on second electrode 208 is exposed at the bottom of opening 209a, and first step 121 is formed as third step 223 formed by first contact plug 204 and second insulating film 203 adjacent to first contact plug 204 is transferred onto second electrode 208. First step 221 is of a downwardly convex shape. In this example, it is not essential that first step 221 be exposed on the upper surface of second electrode 208. It suffices that first step 221 be formed at a portion located within opening 209a, as viewed in plan view, at an interface between metal oxide layer 206 and second electrode 208.

Metal oxide layer 206 is a layer whose resistance value changes reversibly in accordance with an electrical signal given across first electrode 205 and second electrode 208. For example, metal oxide layer 206 transitions reversibly between a high-resistance state and a low-resistance state in accordance with the voltage applied across first electrode 205 and second electrode 208 and the presence or absence of a hydrogen-containing gas in a gas that comes into contact with second electrode 208.

Local region 207 is present inside metal oxide layer 206, and local region 207 is in contact with second electrode 208 but is not in contact with first electrode 205.

In this example, local region 207 is a small region that includes a filament formed of an oxygen vacant site, and the filament functions as an electrically conductive path.

To be more specific, metal oxide layer 206 is formed of a metal oxide, and the degree of oxygen deficiency of a metal oxide included in local region 207 of metal oxide layer 206 is greater than the degree of oxygen deficiency of a metal oxide included in a portion of metal oxide layer 206 other than local region 207.

The degree of oxygen deficiency of the metal oxide included in local region 207 changes reversibly in accordance with the voltage applied across first electrode 205 and second electrode 208 and the presence or absence of a hydrogen-containing gas in a gas that comes into contact with second electrode 208 via opening 209a.

Gas sensor 200 configured as described above can provide the following advantageous effects.

As an initial breakdown voltage is applied, local region 207 that is in contact with second electrode 208 but is not in contact with first electrode 205 is formed within metal oxide layer 206, as illustrated in FIG. 8A.

In this example, as in Embodiment 1, local region 207 is produced so as to be concentrated in a portion near first step 221 on metal oxide layer 206, where first step 221 is formed as third step 223 formed between first contact plug 204 and second insulating film 203 is transferred onto metal oxide layer 206.

This is because when the initial breakdown voltage is applied across first electrode 205 and second electrode 208, the electric field is enhanced near the step on metal oxide layer 206 and thus local region 207 is formed more easily particularly in the region near this step.

Meanwhile, since first contact plug 204 is formed within opening 209a as viewed in plan view, the hydrogen atoms originating from the hydrogen-containing gas dissociated by second electrode 208 reach local region 207 in a short period of time, and thus a gas sensor that excels in the responsiveness can be obtained.

The phenomenon of the resistance change and the mechanism of detecting hydrogen in gas sensor 200 are similar to the phenomenon of the resistance change and the mechanism of detecting hydrogen in gas sensor 100 according to Embodiment 1, and thus repetitive descriptions thereof will be omitted herein.

Method of Manufacturing Gas Sensor

In the following section, an example of a method of manufacturing gas sensor 200 according to the present embodiment will be described with reference to FIGS. 9A to 9J and FIG. 10.

Figure 9A:
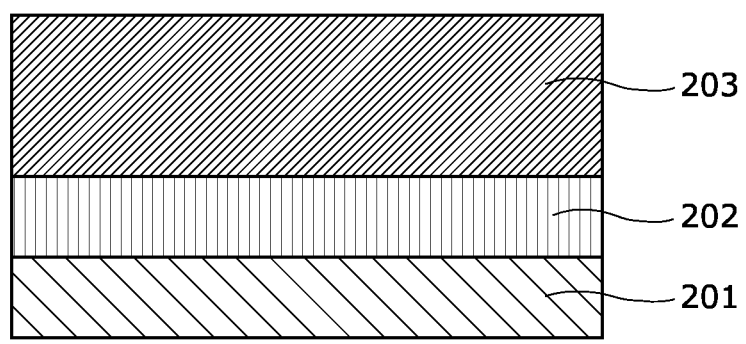
FIG. 9A is a cross-sectional view illustrating a method of manufacturing the gas sensor according to Embodiment 2.

First, as illustrated in FIG. 9A, aluminum is deposited, for example, on silicon substrate 201 to the thickness of, for example, 400 nm. Then, a wiring pattern is patterned through a photolithography technique, the aluminum is etched through a dry etching technique, and the aluminum is processed into a wiring pattern to form first wiring 202. At this point, an insulating film formed, for example, through a CVD technique may be interposed between first wiring 202 and silicon substrate 201. First wiring 202 can also be formed of copper, instead of aluminum, or an adhesive layer made of titanium, titanium nitride, or the like, may also be formed on top of and under the aluminum.

Then, a silicon oxide film is deposited on first wiring 202 through, for example, a CVD technique, to the thickness of 500 nm to form second insulating film 203. In this case, second insulating film 203 may have a layered structure of a silicon oxide film and a silicon nitride film.

Figure 9B:
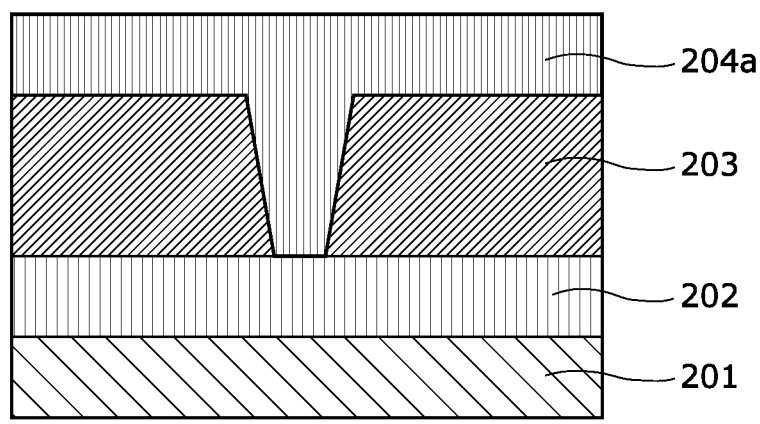
FIG. 9B is another cross-sectional view illustrating the method of manufacturing the gas sensor according to Embodiment 2.

Next, a mask patterned into a hole shape is disposed on second insulating film 203 through a photolithography technique, and then a hole penetrating through second insulating film 203 and reaching first wiring 202 is formed by use of the stated mask through a dry etching technique (not illustrated). Thereafter, as illustrated in FIG. 9B, tungsten is deposited on the entire surface of the wafer to the thickness of 800 nm through a CVD technique, and first contact plug film 204a is deposited within the hole so as to be in contact with first wiring 202. First contact plug film 204a may be made of copper, or an adhesive layer and a barrier layer made of titanium, titanium nitride, tantalum, tantalum nitride, or the like can be formed between first contact plug film 204a made of tungsten, copper, or the like and first wiring 202 and second insulating film 203.

Figure 9C:
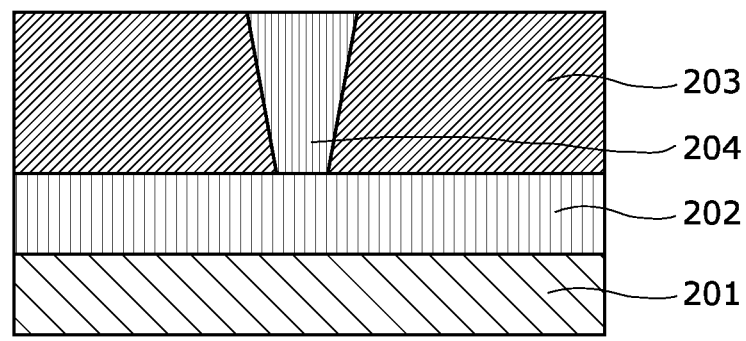
FIG. 9C is another cross-sectional view illustrating the method of manufacturing the gas sensor according to Embodiment 2.

Next, as illustrated in FIG. 9C, first contact plug film 204a is polished through a CMP technique to expose second insulating film 203, and first contact plug 204 is formed inside the hole.

The surface of first contact plug film 204a is set to be at least level with or lower than the surface of surrounding second insulating film 203.

Figure 9D:
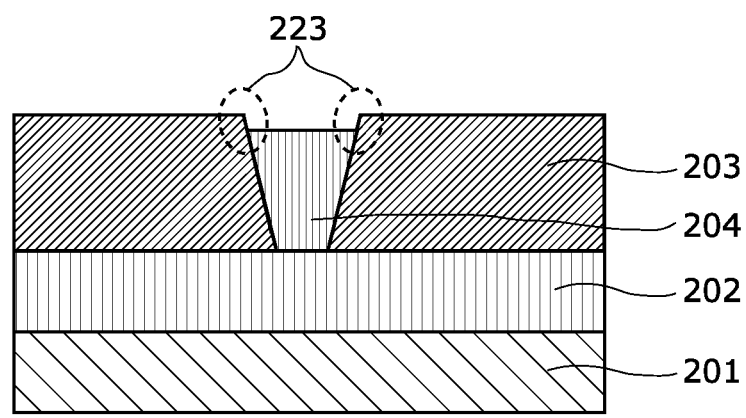
FIG. 9D is another cross-sectional view illustrating the method of manufacturing the gas sensor according to Embodiment 2.

Next, as illustrated in FIG. 9D, W is etched, for example, by 30 nm through a dry etching technique, and the surface of the upper portion of first contact plug 204 is formed so as to lie lower than the surface of second insulating film 203 surrounding first contact plug 204. In this manner, as with the gas sensor according to Embodiment 1, third step 223 is formed at the border between first contact plug 204 and second insulating film 203. What differs from Embodiment 1 is that third step 223 is formed without etching second insulating film 203 having a large surface area.

Figure 9E:
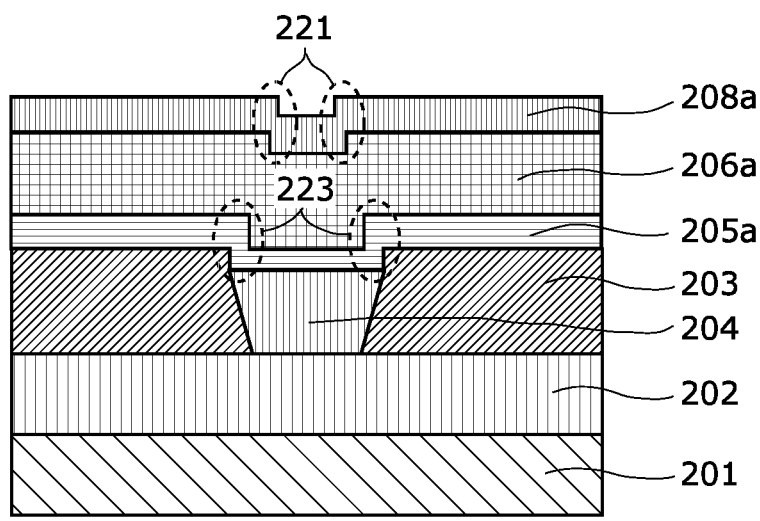
FIG. 9E is another cross-sectional view illustrating the method of manufacturing the gas sensor according to Embodiment 2.

Next, as illustrated in FIG. 9E, as first electrode film 205a, a tantalum nitride film having a thickness of, for example, 30 nm is formed so as to cover the surface of second insulating film 203 and the surface of first contact plug 204 recessed from the surface of second insulating film 203 through a sputtering technique. At this point, first electrode film 205a may be a laminated film of titanium, titanium nitride, or the like. Next, metal oxide film 206a having a thickness of 30 nm is formed on first electrode film 205a through a reactive sputtering technique in which, for example, tantalum is used as a target. Next, as second electrode film 208a, a platinum film having a thickness of, for example, 10 nm is formed on metal oxide film 206a through a sputtering technique. In this example, the film thickness of the platinum film is desirably no less than 5 nm nor greater than 200 nm.

Through the above processes, third step 223 between the surface of second insulating film 203 and the surface of first contact plug 204 formed so as to be recessed downward from the surface of surrounding second insulating film 203 is transferred to first electrode film 205a, metal oxide film 206a, and second electrode film 208a, and this results in a structure having first step 221 formed on second electrode film 208a near the border region between first contact plug 204 and second insulating film 203.

Figure 9F:
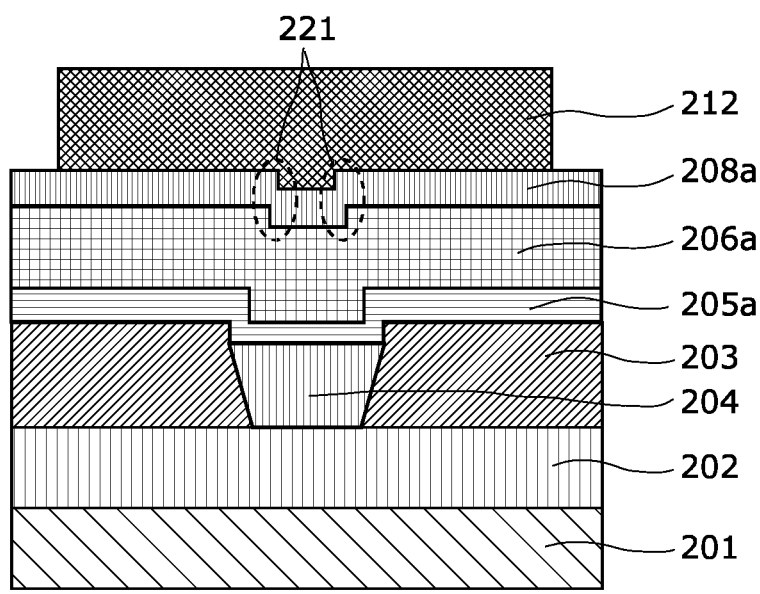
FIG. 9F is another cross-sectional view illustrating the method of manufacturing the gas sensor according to Embodiment 2.

Next, as illustrated in FIG. 9F, through, for example, a photolithography technique, first mask 212 composed of photoresist is formed into the shape of the sensor on second electrode film 208a that includes first step 221 as viewed in plan view. The dimensions of first mask 212 formed at this point may be, for example, from 1 μm on each side to 8 μm on each side.

Figure 9G:
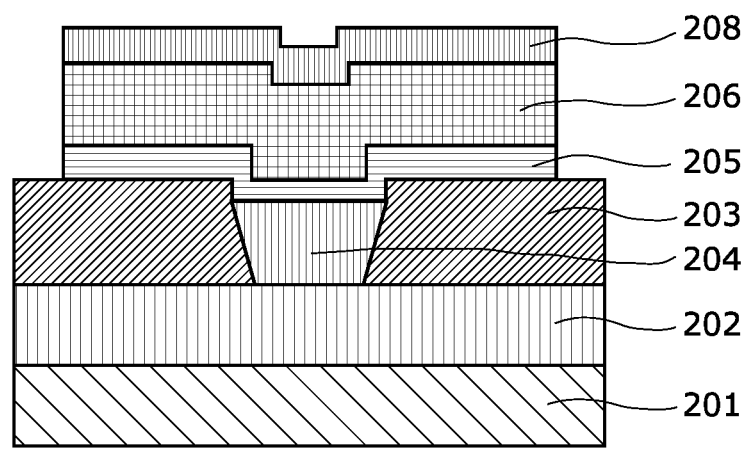
FIG. 9G is another cross-sectional view illustrating the method of manufacturing the gas sensor according to Embodiment 2.

Next, as illustrated in FIG. 9G, first electrode film 205a, metal oxide film 206a, and second electrode film 208a are patterned into the shape of the gas detecting element through a dry etching technique in which first mask 212 is used, and thus the gas detecting element including first electrode 205, metal oxide layer 206, and second electrode 208 is formed.

Figure 9H:
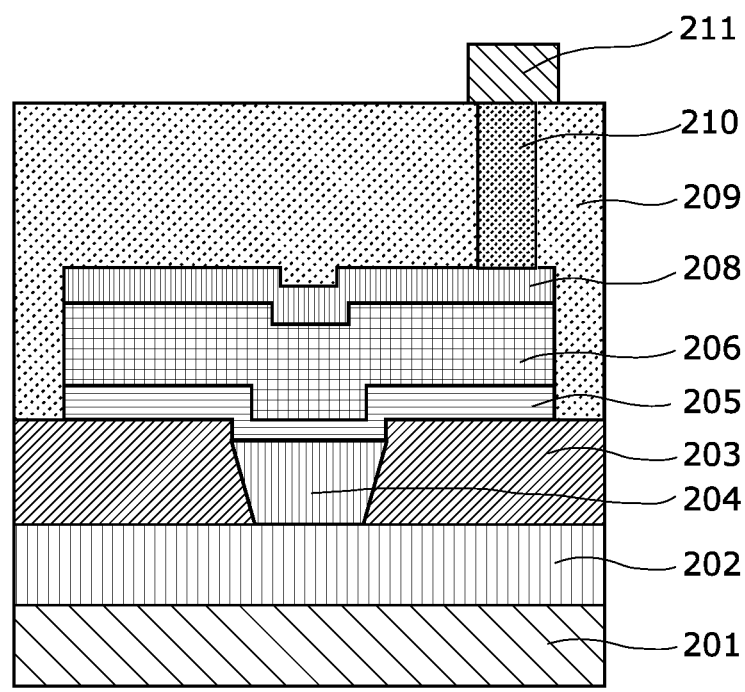
FIG. 9H is another cross-sectional view illustrating the method of manufacturing the gas sensor according to Embodiment 2.

Next, as illustrated in FIG. 9H, as first insulating film 209, a silicon oxide film having a thickness of, for example, 800 nm is formed so as to cover at least a part of metal oxide layer 206 and a part of second electrode 208. Thereafter, the upper portion of first insulating film 209 is polished by 300 nm through a CMP technique to flatten the surface of first insulating film 209. Thereafter, a via hole penetrating through first insulating film 209 and reaching a part of second electrode 208 is formed through an etching technique, tungsten is deposited on the entire surface of the wafer to the thickness of 800 nm through a CVD technique, and then the tungsten is flattened so as to remain only inside the plug through a CMP technique. Thus, second contact plug 210 is formed. Thereafter, another conductive film is deposited on first insulating film 209 and patterned, and thus second wiring 211 connected to second contact plug 210 is formed.

Figure 9I:
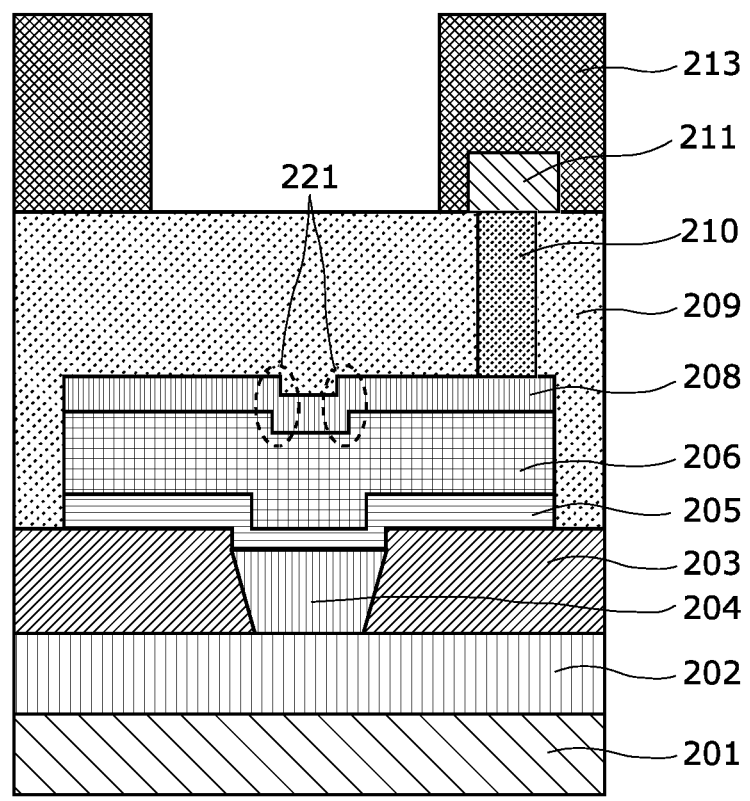
FIG. 9I is another cross-sectional view illustrating the method of manufacturing the gas sensor according to Embodiment 2.

Next, as illustrated in FIG. 9I, second mask 213 composed of photoresist is formed on first insulating film 209 through a lithography technique. At this point, as viewed in plan view, the opening in second mask 213 is formed into a shape that includes the entirety of first step 221 formed on second electrode 208 within second electrode 208.

Figure 9J:
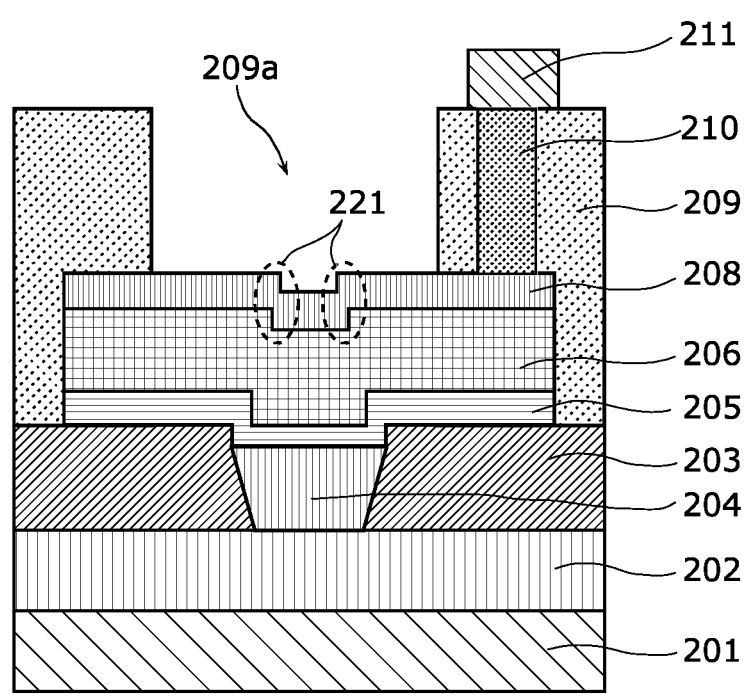
FIG. 9J is another cross-sectional view illustrating the method of manufacturing the gas sensor according to Embodiment 2.

Next, as illustrated in FIG. 9J, first insulating film 209 is etched by use of second mask 213 through a dry etching technique, and opening 209a exposing a part of the surface of second electrode 208 is formed.

Figure 10:
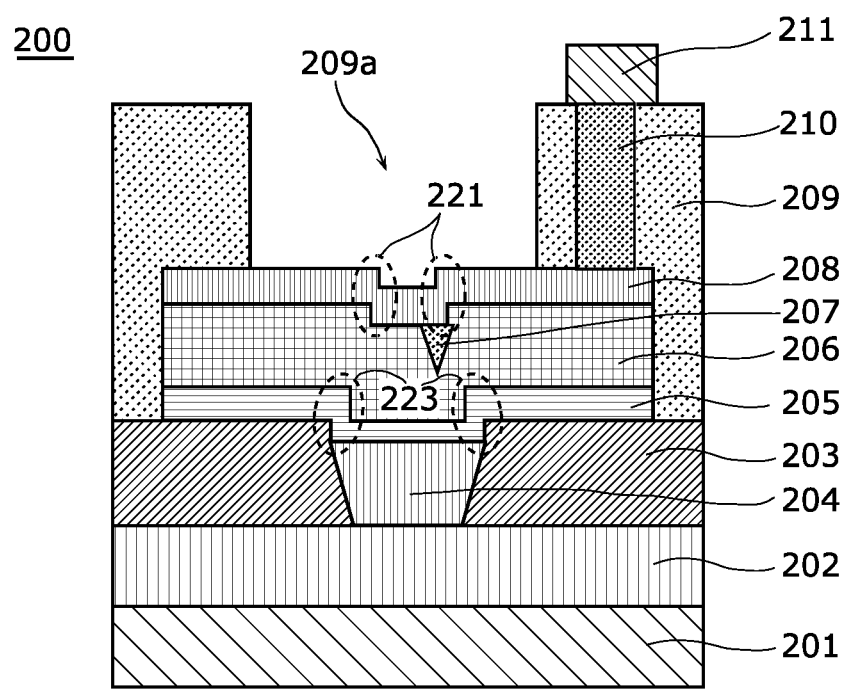
FIG. 10 is a cross-sectional view of the gas sensor according to Embodiment 2.

Next, as illustrated in FIG. 10, an initial breakdown voltage is applied across first electrode 205 and second electrode 208 in gas sensor 200 to form local region 207 within metal oxide layer 206, and thus gas sensor 200 is completed.

As described above, local region 207 is generated concentratedly in metal oxide layer 206 near first step 221 formed as third step 223 formed between first contact plug 204 and second insulating film 203 is transferred onto metal oxide layer 206. Specifically, local region 207 is generated concentratedly near first step 221 formed on second electrode 208.

The resistance change characteristic associated with the voltage application in gas sensor 200 configured as described above is similar to the resistance change characteristic associated with the voltage application in gas sensor 100 described with reference to FIGS. 4 and 5.

Moreover, with regard to the mechanism of the resistance change in gas sensor 200 caused by a hydrogen-containing gas as well, the resistance change occurs by a hydrogen-containing gas through a mechanism similar to the mechanism described regarding gas sensor 100.

As described thus far, with gas sensor 200 according to the present embodiment, gas sensor 200 does not need to be heated by a heater separately, and a hydrogen-containing gas can be detected stably. Thus, a gas sensor that excels in the power saving performance can be obtained.

Embodiment 3

A fuel cell vehicle according to Embodiment 3 includes any one of the gas sensors described above according to Embodiment 1, Embodiment 2, and their variations and detects a hydrogen gas inside the vehicle by use of that gas sensor.

Figure 11:
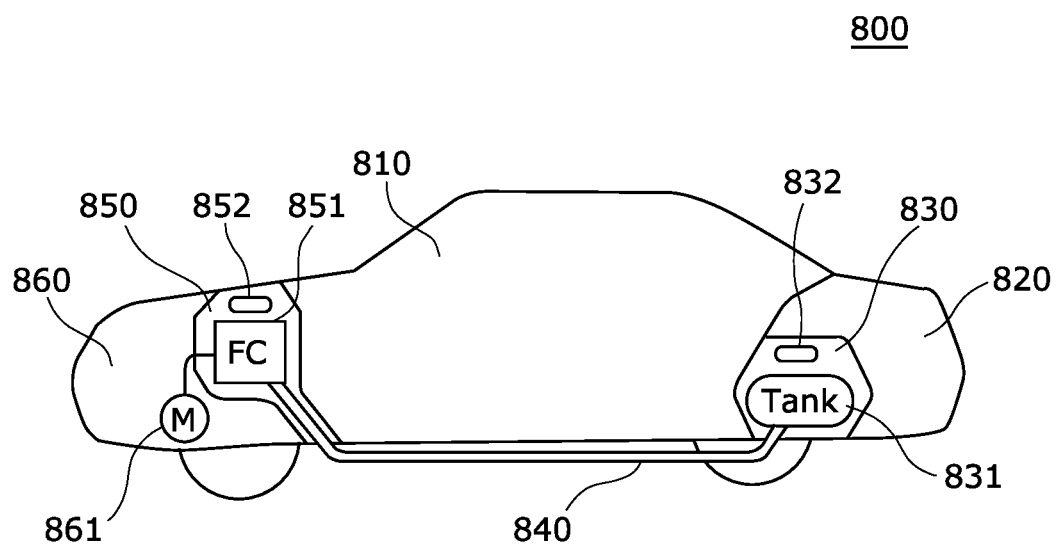
FIG. 11 is a side view of a fuel cell vehicle according to Embodiment 3.

FIG. 11 is a side view illustrating an example of a configuration of fuel cell vehicle 800 according to Embodiment 3.

Fuel cell vehicle 800 includes passenger compartment 810, luggage compartment 820, gas tank compartment 830, fuel tank 831, gas sensor 832, pipe 840, fuel cell compartment 850, fuel cell 851, gas sensor 852, motor compartment 860, and motor 861.

Fuel tank 831 is provided inside gas tank compartment 830 and holds a hydrogen gas as a fuel gas. In this example, gas sensor 832 detects a fuel gas leakage in gas tank compartment 830.

Fuel cell 851 includes a fuel cell stack in which a plurality of cells serving as base units having a fuel pole, an air pole, and an electrolyte are stacked on top of each other. Fuel cell 851 is provided inside fuel cell compartment 850. The hydrogen gas inside fuel tank 831 is fed to fuel cell 851 inside fuel cell compartment 850 via pipe 840. This hydrogen gas and an oxygen gas in the atmospheric air are made to react inside fuel cell 851, and thus electricity is generated. In this example, gas sensor 852 detects a hydrogen gas leakage in fuel cell compartment 850.

Motor 861 is provided inside motor compartment 860. Fuel cell vehicle 800 runs as motor 861 rotates on the power generated by fuel cell 851. As described above, in one example, a gas sensor according to the present disclosure can detect a hydrogen-containing gas with very small power consumption of around 0.01 mW. Therefore, by utilizing this excellent power saving performance of the gas sensor, a hydrogen gas leakage can be monitored continuously without a large increase in the standby power of the fuel cell vehicle.

For example, a predetermined voltage may be applied continuously to each of gas sensor 832 and gas sensor 852 regardless of the operation state of the ignition key in fuel cell vehicle 800, and whether any hydrogen gas is present outside fuel tank 831 in gas tank compartment 830 and outside fuel cell 851 in fuel cell compartment 850 may be determined based on the amount of the current that flows in each of gas sensor 832 and gas sensor 852.

With this configuration, for example, since the presence or absence of a hydrogen gas leakage has already been determined when the ignition key is operated, the time it takes to start the fuel cell vehicle can be reduced as compared to a case where a gas sensor is driven to determine the presence or absence of a hydrogen gas leakage after the ignition key has been operated. Moreover, the above configuration can continue to monitor a hydrogen gas leakage, for example, even after the fuel cell vehicle has been stored into a garage after having been driven. Thus, the safety can be improved.

Thus far, a gas sensor, a method of detecting a hydrogen gas, and a fuel cell vehicle according to some aspects of the present disclosure have been described based on some embodiments, but the present disclosure is not limited to these embodiments. Unless departing from the spirit of the present disclosure, an embodiment obtained by making various modifications that are conceivable by a person skilled in the art to the present embodiments or an embodiment obtained by combining constituent elements in the foregoing embodiments is also encompassed by the scope of the present disclosure.

For example, the gas sensor described above may further include a measuring circuit that measures the current that flows in a metal oxide layer when a predetermined voltage is applied across a first electrode and a second electrode.

Moreover, the gas sensor described above may further include a power supply circuit that applies a predetermined voltage continuously across a first electrode and a second electrode.

With such a configuration, a highly utilizable gas sensor can be obtained as a module component including a measuring circuit or a power supply circuit.

Although only some exemplary embodiments of the present disclosure have been described in detail above, those skilled in the art will readily appreciate that many modifications are possible in the exemplary embodiments without materially departing from the novel teachings and advantages of the present disclosure. Accordingly, all such modifications are intended to be included within the scope of the present disclosure.

INDUSTRIAL APPLICABILITY

A gas sensor according to the present disclosure functions as a gas sensor that excels in the power saving performance and finds its effective use as a hydrogen sensor used in a fuel cell vehicle or the like, for example.

The invention claimed is:
1. A gas sensor, comprising:
a gas detecting element that includes a first electrode, a metal oxide layer provided on the first electrode, and a second electrode provided on the metal oxide layer, the gas detecting element detecting a gas molecule existing in a gas and including a hydrogen atom; and
a first insulating film having an opening that allows a part of the second electrode to be exposed therethrough, the first insulating film covering the first electrode, the metal oxide layer, and another part of the second electrode, wherein the metal oxide layer has a characteristic in which a resistance value of the metal oxide layer changes when the second electrode comes into contact with the gas molecule, a first step is provided at a portion lying on an interface between the metal oxide layer and the second electrode and located within the opening as viewed in plan view, a local region is provided in the metal oxide layer and close to the first step, a degree of oxygen deficiency of the local region is greater than a degree of oxygen deficiency of a region other than the local region in the metal oxide layer, and in the plan view, the first electrode is larger than the first step.

2. The gas sensor according to claim 1, wherein the first step is of an upwardly convex shape.

3. The gas sensor according to claim 2, further comprising:

a first contact plug provided between a substrate and the first electrode, wherein the first contact plug includes a side surface surrounding the first contact plug, and the side surface is covered by a second insulating film, the first contact plug has an upper surface that projects from an upper surface of the second insulating film, the first electrode includes a second step provided across the upper surface of the first contact plug and the upper surface of the second insulating film surrounding the first contact plug, and the first step is a step resulting from a transfer of the second step onto an upper surface of the metal oxide layer.

4. The gas sensor according to claim 1, wherein the first step is of a downwardly convex shape.

5. The gas sensor according to claim 4, further comprising:

a first contact plug provided between a substrate and the first electrode, wherein a side surface surrounding the first contact plug is covered by a second insulating film, an upper surface of the first contact plug is recessed from an upper surface of the second insulating film, the first electrode includes a third step provided across the upper surface of the first contact plug and the upper surface of the second insulating film surrounding the first contact plug, and the first step is a step resulting from a transfer of the third step onto an upper surface of the metal oxide layer.

6. The gas sensor according to claim 1, wherein the second electrode includes a material having a catalytic effect of dissociating the gas molecule into the hydrogen atom.

7. The gas sensor according to claim 6, wherein the second electrode includes platinum or palladium.

8. The gas sensor according to claim 1, wherein the metal oxide layer transitions reversibly between a high-resistance state and a low-resistance state in accordance with a voltage applied across the first electrode and the second electrode.

9. The gas sensor according to claim 1, further comprising:

a current detector that detects a current that flows in the metal oxide layer when a predetermined voltage is applied across the first electrode and the second electrode, wherein a decrease in the resistance value is detected based on an increase in the current detected by the current detector.

10. The gas sensor according to claim 1, wherein the metal oxide layer includes a transition metal oxide.

11. The gas sensor according to claim 10, wherein the transition metal oxide is any one of tantalum oxide, hafnium oxide, or zirconium oxide.

12. The gas sensor according to claim 1, further comprising:

a second contact plug penetrating through a part of a portion of the first insulating film where the first insulating film covers the second electrode and connected to the second electrode; and a conductor connected to the second contact plug at an upper side of the second contact plug.

13. A fuel cell vehicle, comprising:

a passenger compartment;

a gas tank compartment housing a hydrogen gas tank;

a fuel cell compartment housing a fuel cell; and the gas sensor according to claim 1, wherein the gas sensor is provided in at least one of the gas tank compartment or the fuel cell compartment.

* * * * *